US009034876B2

(12) United States Patent
Dobrzanski et al.

(10) Patent No.: US 9,034,876 B2
(45) Date of Patent: *May 19, 2015

(54) TREATMENT OF CHRONIC INFLAMMATION WITH A 1,2,4-TRIAZOLO [1,5A] PYRIDINE DERIVATIVE

(71) Applicant: Cephalon, Inc., Frazer, PA (US)

(72) Inventors: Pawel T. Dobrzanski, Downingtown, PA (US); Matthew M. Seavey, Secane, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/911,465

(22) Filed: Jun. 6, 2013

(65) Prior Publication Data

US 2013/0267535 A1 Oct. 10, 2013

Related U.S. Application Data

(63) Continuation of application No. PCT/US2011/063272, filed on Dec. 5, 2011.

(60) Provisional application No. 61/420,078, filed on Dec. 6, 2010.

(51) Int. Cl.
*A61K 31/496* (2006.01)
*A61K 45/06* (2006.01)

(52) U.S. Cl.
CPC .............. *A61K 31/496* (2013.01); *A61K 45/06* (2013.01)

(58) Field of Classification Search
CPC ............................ A61K 31/496; A61K 45/06
See application file for complete search history.

(56) References Cited

U.S. PATENT DOCUMENTS

2010/0029675 A1* 2/2010 Hwang .................... 514/252.18
2010/0311693 A1 12/2010 Curry et al.

FOREIGN PATENT DOCUMENTS

WO   WO2009/155565 A1   12/2009
WO   WO2010/141796 A2   12/2010

OTHER PUBLICATIONS

Al-Janadi et al. (J of Clinical Immunology, 13, 1, 1993).*
Alonzi et al., "Interleukin 6 is Required for the Development of Collagen-induced Arthritis", *J. Exp. Med.* (1998), vol. 187, pp. 461-468.
Bajpai, "Fostamatinib, a Syk inhibitor prodrug for the treatment of inflammatory diseases", *IDrugs* (2009), vol. 12, pp. 174-185.
Bingham, "Emerging Therapeutics for Rheumatoid Arthritis", *Bull. NYU Hosp. for Joint Diseases* (2008), vol. 66, pp. 210-215.
Bradshaw, The Src, Syk, and Tec family kinases: Distinct types of molecular switches, *Cellular Signalling* (2010), vol. 22, pp. 1175-1184.
Brand et al., "The Mouse Model of Collagen-Induced Arthritis", *Methods in Molecular Medicine* (2004), vol. 102, pp. 295-312.
Calero et al., "B Cell Therapies for Rheumatoid Arthritis: Beyond B cell Depletion," *Rheum. Dis. Clin. N. Amer.* (2010), vol. 36, pp. 325-343.
Chan et al., "Therapeutic antibodies for autoimmunity and inflammation," *Nat. Rev. Immunology* (2010), vol. 10, pp. 301-316.
Church et al., "Primer: inflammasomes and interleukin 1β in inflammatory disorders," *Nat. Clin. Prac. Rheumatology* (2008), vol. 4, pp. 34-42.
Cohen et al., "Kinase Inhibitors: a new approach to rheumatoid arthritis treatment", *Curr. Opin. Rheumatology* (2010), vol. 22, pp. 330-335.
Cornelissen et al., "The IL-12/IL-23 axis and its role in Th17 cell development, pathology and plasticity in arthritis," *Curr. Opin. Invest. Drugs* (2009), vol. 10, pp. 452-462.
Douni et al., "Attenuation of inflammatory polyarthritis in TNF transgenic mice by diacerein: comparative analysis with dexamethasone, methotrexate and anti-TNF protocols", *Arthritis Res. Ther.* (2004), vol. 6, pp. R65-R72.
Eggert et al., "Rapid Demineralization in Acidic Buffers," *Histochemistry* (1979), vol. 59, pp. 215-224.
Ellis et al., "Activation of the transcription factor NF-KB in the rat air pouch model of inflammation," *Ann. Rheum. Dis.* (2000), vol. 59, pp. 303-307.
Fabian et al., "A small molecular-kinase interaction map for clinical kinase inhibitors", *Nat. Biotech.* (2005), vol. 23, pp. 329-336.
Fonseca et al., "Interleukin-6 as a key player in systemic inflammation and joint destruction," *Autoimmunity Rev.* (2009), vol. 8, pp. 538-542.
Fowell et al., "Impaired NFATc Translocation and Failure of Th2 Development in Itk-Deficient CD4 T Cells," *Immunity* (1999), vol. 11, pp. 399-409.
Fridman et al., "Selective Inhibition of JAK1 and JAK2 is Efficacious in Rodent Models of Arthritis: Preclinical Characterization of INCB028050," *J. Immunology* (2010), vol. 184, pp. 5298-5307.
Fuhrer et al., "Complex Formation of JAK2 and PP2A, PI3K, and Yes in Response to the Hematopoietic Cytokine Interleukin-11," *Biochem. and Biophys. Res. Comm.* (1996), vol. 224, pp. 289-296.
Gaestel et al., "Targeting innate immunity protein kinase signaling in inflammation", *Nat. Rev. Drug Discovery* (2009), vol. 8, pp. 480-499.
Ghoreschi et al., "Selectivity and herapeutic inhibition of kinases: to be or not to be?," *Nat. Immunology* (2009), vol. 10, pp. 356-360.
Goldbach-Mansky et al., "New Concepts in the Treatment of Rheumatoid Arthritis," *Annu. Rev. Med.* (2003), vol. 54, pp. 197-216.
Haan et al., "SOCS-mediated downregulation of mutant JAK2 (V617F, T875N and K539L) counteracts cytokine-independent signaling," *Oncogene* (2009), vol. 28, pp. 3069-3080.
Haubert et al., "Vav1 couples the T cell receptor to cAMP response element activation via a PKC-dependent pathway," *Cell. Signalling* (2010), vol. 22, pp. 944-954.
Hexner et al., "Lestaurtinib (CEP701) is a JAK2 inhibitor that suppresses JAK2/STAT5 signaling and the proliferation of primary erythroid cells from patients with myeloproliferative disorders," *Blood* (2008), vol. 111, pp. 5663-5671.

(Continued)

*Primary Examiner* — Uma Ramachandran

(57) ABSTRACT

This application describes and provides a method of treating diseases or disorders characterized by chronic systemic inflammation, such as rheumatoid arthritis, using a compound that inhibits JAK2 kinase.

15 Claims, 35 Drawing Sheets

(56) References Cited

OTHER PUBLICATIONS

Holmdahl, "Primer: comparative genetics of animal models of arthritis—a tool to resolve complexity" *Nat. Clin. Prac. Rheumatology* (2007), vol. 3, pp. 104-111.
Imboden, "The Immunopathogenesis of Rheumatoid Arthritis," *Ann. Rev. Pathol. Mech. Dis.* (2009), vol. 4, pp. 417-434.
Isomaki et al., "The expression of SOCS is altered in rheumatoid arthritis," *Rheumatology* (2007), vol. 46, pp. 1538-1546.
Kagari et al., "The Importance of IL-1β and TNF-α and the Noninvolvement of IL-6, in the Development of Monoclonal Antibody-Induced Arthritis," *J. Immunology* (2002), vol. 169, pp. 1459-1466.
Kang et al., "Modulation of collagen-induced arthritis by IL-4 and dexamethasone: the synergistic effect of IL-4 and dexamethasone on the resolution of CIA," *Immunopharmacology* (2000), vol. 49, pp. 317-324.
Karaman et al., "A quantitative analysis of kinase inhibitor selectivity," *Nat. Biotech.* (2008), vol. 26, pp. 127-132.
Kerbleski et al., "Dermatological complications and safety of anti-TNF treatments," *Gut* (2009), vol. 58, pp. 1033-1039.
Kiss et al., "Recent Developments on JAK2 inhibitors: a patent review," *Expert Opinion on Therapeutic Patents* (2010), vol. 20, pp. 471-495.
Kundu et al., "Inflammation: Gearing the journey to cancer," *Mutation Res.* (2008), vol. 659, pp. 15-30.
Lacava et al., "The Weight of Leptin in Immunity," *Nat. Rev. Immunology* (2004), vol. 4, pp. 371-379.
Lo et al., "Nuclear interaction of EGFR and STAT3 in the activation of the iNOS/NO pathway," *Cancer Cell* (2005), vol. 7, pp. 575-589.
Lu et al., "Novel Method of Monitoring Trace Cytokines and Activated STAT Molecules in the Paws of Arthritic Mice Using Multiplex Bead Technology," *BMC Immunology* (2010), pp. 1-11.
McCulloch et al., Signalling platforms that modulate the inflammatory response: new targets for drug development, *Nat. Rev. Drug Discovery* (2006), vol. 5, pp. 864-876.
McInnes et al., "Cytokines in the pathogenesis of rheumatoid arthritis," *Nat. Rev. Immunology* (2007), vol. 7, pp. 429-442.
Montesinos et al., "Suppression of inflammation by low-dose methotrexate is mediated by adenosine $A_{2A}$ receptor but not $A_3$ receptor activation in thioglycollate-induced peritonitis," *Arthritis Res. & Therapy* (2006), vol. 8, R53.
Mueller et al., "Attenuation of Immunological Symptoms of Allergic Asthma in Mice Lacking the Tyrosine Kinase ITK," *J. Immunology* (2003), vol. 170, pp. 5056-5063.
Nathan et al., "Nonresolving Inflammation", *Cell* (2010), vol. 140, pp. 871-882.
"Dipping into Incyte's JAK-pot", *Nat. Rev. Drug Discovery* (2010), vol. 9, p. 94.
Oldfield et al., "Tocilizumab—A review of its use in the Management of Rheumatoid Arthritis," *Drugs* (2009), vol. 69, pp. 609-632.
Olsen et al., "New Drugs for Rheumatoid Arthritis," *N. Engl. J. Med.* (2004), vol. 350, pp. 2167-2179.
Opar, "Kinase inhibitors attract attention as oral rheumatoid arthritis drugs," *Nat. Rev. Drug Discovery* (2010), vol. 2010, pp. 257-258.
O'Shea et al., "Cytokine Signaling Modules in Inflammatory Responses," *Immunity* (2008), vol. 28, pp. 477-487.
O'Shea et al., "A New Modality for Immunosuppression: Targeting the JAK/STAT Pathway," *Nat. Rev. Drug Discovery* (2004), vol. 3, pp. 555-564.

Procaccini et al., "Leptin Signaling: A Key Pathway in Immune Responses," *Curr. Signal Tranduction Therapy* (2009), vol. 4, pp. 22-30.
Ramos-Casals et al., "Autoimmune diseases induced by TNF-targeted therapies," *Best Prac. & Res. Clin. Rheumatology* (2008), vol. 22, pp. 847-861.
Romano et al., "Carrageenan-induced acute inflammation in the mouse air pouch synovial model. Role of tumour necrosis factor," *Mediators of Inflammation* (1997), vol. 6, pp. 32-38.
Ryu et al., "Regulation of Neutrophil Adhesion by Pituitary Growth Hormone Accompanies Tyrosine Phosphorylation of JAK2 p125$^{FAK}$, and Paxillin," *J. Immunology* (2000), vol. 165, pp. 2116-2123.
Sasai et al., "Delayed Onset and Reduced Severity of Collagen-Induced Arthritis in Interleukin-6-Deficient Mice," *Arthritis & Rheumatism* (1999), vol. 42, pp. 1635-1643.
Sayeski et al., "A Catalytically Active JAK2 is Required for the Angiotensin II-dependent Activation of Fyn," *J. Biological Chem.* (1999), vol. 274, pp. 33131-33142.
Seavey et al., "An Anti-Vascular Endothelial Growth Factor Receptor 2/Fetal Liver Kinase-1 *Listeria monocytogenes* Anti-Angiogenesis Cancer Vaccine for the Treatment of Primary and Metastatic Her-2/neu+ Breast Tumors in a Mouse Model[1]", *J. Immunology* (2009), vol. 182, pp. 5537-5546.
Sefton et al., "Role of tyrosine kinases in lymphocyte activation," *Curr. Opin. Immunology* (1994), vol. 6, pp. 372-379.
Shigematsu et al., "Role of the *vav* Proto-oncogene Product (Vav) in Erythropoietin-mediated Cell Proliferation and Phosphatidylinositol 3-Kinase Activity," *J. Biological Chem.* (1997), vol. 272, pp. 14334-14340.
Singh et al., "Th1/Th17 Cytokine Profiles in Patients with Reactive Arthritis/Undifferentiated Spondyloarthropathy," *J. Rheumatol.* (2007), vol. 34, pp. 2285-2290.
Stump et al., "A highly selective, orally active inhibitor of Janus kinase 2, CEP-33779, ablates disease in two mouse models of rheumatoid arthritis," *Arthritis Research & Therapy* (2011), vol. 13, R68, pp. 1-15.
Takahashi-Tezuka et al., "Tec tyrosine kinase links the cytokine receptors to PI-3 kinase probably through JAK," *Oncogene* (1997), vol. 14, pp. 2273-2282.
Turkson et al., "Stat3 Activation by Src Induces Specific Gene Regulation an is Required for Cell Transformation," *Molecular and Cellular Biology* (1998), vol. 18, pp. 2545-2552.
Uchiyama et al., "Tocilizumab, a Humanized Anti-interleukin-6 Receptor Antibody, Ameliorates Joint Swelling in Established Monkey Collagen-Induced Arthritis," *Biol. Pharm. Bull.* (2008), vol. 31, pp. 1159-1163.
Verdenius et al., "A Quantitative Study of Decalcification Methods in Histology," *J. Clin. Path.* (1958), vol. 11, pp. 229-236.
Vingsbo et al., "Association of Pepsin with Type II Collagen (CII) Breaks Control of CII Autoimmunity and Triggers Development of Arthritis in Rats," *Scand. J. Immunol.* (1993), vol. 37, pp. 337-342.
Walker et al., "The JAK-STAT Pathway in Rheumatoid Arthritis," *J. Rheumatology* (2005), vol. pp. 1650-1653.
West, "Erratum: CP-690550, a JAK3 inhibitor as an immunosuppressant for the treatment of rheumatoid arthritis, transplant rejection, psoriasis and other immune-mediated disorders," *Curr. Opin. Invest. Drug* (2009), vol. 10, pp. 1004-1006.
Williams et al., "Anti-TNF-induced lupus," *Rheumatology* (2009), vol. 48, pp. 716-720.
Ying et al., "Loss of SOCS3 expression is associated with an increased risk of recurrent disease in breast carcinoma," *J. Cancer Res. Clin. Oncol.* (2010), vol. 136, pp. 1617-1626.

\* cited by examiner

Figure 1A

Enzyme and cellular potency of Compound-A (nM)

| | JAK1 | JAK2 | JAK3 | TYK2 | FAK | c-MET | ALK |
|---|---|---|---|---|---|---|---|
| Enzyme $IC_{50}$ | 80 | 1.6 | 131 | 1552 | 1306 | >10000 | 1494 |
| Cell $IC_{50}$ | ND | 66 | 387 | ND | >10000 | ND | ND |

*Ambit $S(90)_{402}$ = 0.09; Ambit $S(99)_{402}$ = 0.01*

Figure 3D

| | Compound-A | | | | |
|---|---|---|---|---|---|
| | 55mg/kg | 30mg/kg | 10mg/kg | Dex | Vehicle |
| Carpus | | | | | |
| Tarsus | | | | | |

Figure 4D
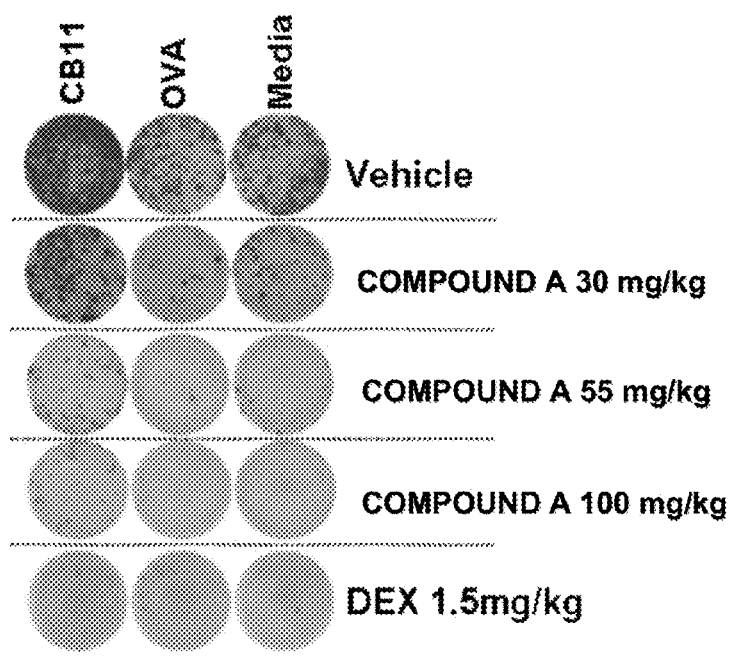
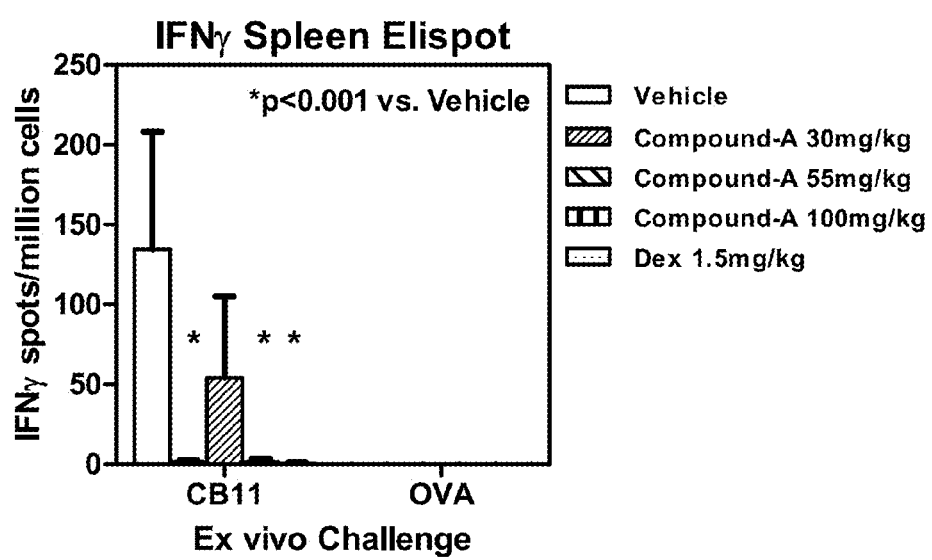

Figure 6
Table I

Tarsus; Mean±SD
CAIA Model

Independent Histopathologist Scores

Score Grade: 0-5

| Group | Proteoglycan loss | Matrix Erosions | Subchondral osteolysis | Osteoproliferation | Synovial Proliferation | Pannus Formation | Inflammation Degree |
|---|---|---|---|---|---|---|---|
| Vehicle | 1.56±0.07 | 3.12±0.71 | 2.50±1.00 | 1.65±0.47 | 2.00±0.81 | 1.12±0.85 | 1.75±0.95 |
| Compound-A 10 mg/kg | 1.39±0.38 | 3.40±2.07 | 2.30±1.30 | 1.70±1.09 | 2.40±1.34 | 1.30±0.97 | 1.60±1.14 |
| Compound-A 30 mg/kg | 1.12±0.88 | 0.75±0.95 | 0.62±0.47* | 0.87±0.62 | 0.25±0.50* | 0.00±0.00 | 0.12±0.25* |
| Compound-A 55 mg/kg | 2.05±0.07 | 0.70±0.44* | 0.60±0.41** | 0.30±0.72* | 0.30±0.44* | 0.00±0.00* | 0.20±0.27* |
| Dex 1.5 mg/kg | 0.98±0.44 | 1.00±0.79 | 0.50±0.35** | 0.70±0.44 | 0.40±0.54* | 0.10±0.22 | 0.30±0.44* |

Compared to Vehicle   *$p<0.05$   $p<0.01$   *$p<0.001$

Figure 7
Table II

Tarsus; Mean±SD
CIA Model

Independent Histopathologist Scores  Score Grade: 0-5

| Group | Proteoglycan loss | Matrix Erosions | Subchondral osteolysis | Osteoproliferation | Synovial Proliferation | Pannus Formation | Inflammation Degree |
|---|---|---|---|---|---|---|---|
| Vehicle | 3.00±0.00 | 3.67±1.52 | 2.50±0.50 | 2.66±0.57 | 2.66±0.57 | 1.66±0.57 | 2.83±0.28 |
| Compound-A 30 mg/kg | 2.50±0.57 | 4.62±0.75 | 2.75±0.50 | 2.50±0.40 | 2.75±0.50 | 2.37±0.94 | 2.12±0.25 |
| Compound-A 55 mg/kg | 1.83±0.76 | 2.83±1.60 | 1.33±1.04 | 1.83±1.15 | 1.00±0.86 | 0.83±0.76 | 0.66±0.57* |
| Compound-A 100 mg/kg | 1.83±0.28 | 2.33±1.52 | 1.50±0.50 | 1.66±0.57 | 1.50±0.86 | 0.66±1.15 | 1.33±0.57** |
| Dex 1.5 mg/kg | 2.25±0.95 | 3.12±2.09 | 1.37±0.94 | 1.50±1.08 | 1.25±0.86 | 0.75±0.64 | 1.00±0.81** |

Compared to Vehicle  *$p<0.05$  $p<0.01$  *$p<0.001$

TREATMENT OF CHRONIC INFLAMMATION WITH A 1,2,4-TRIAZOLO [1,5A] PYRIDINE DERIVATIVE

CROSS REFERENCE TO RELATED APPLICATIONS

This application is a continuation of International Application No. PCT/US2011/063272, filed Dec. 5, 2011, which claims the benefit of U.S. Provisional Application No. 61/420,078, filed Dec. 6, 2010, the disclosures of which are incorporated herein by reference in their entireties.

SUMMARY

This application relates to a 1,2,4-Triazolo[1,5a]Pyridine derivative (Compound A) having the following structure:

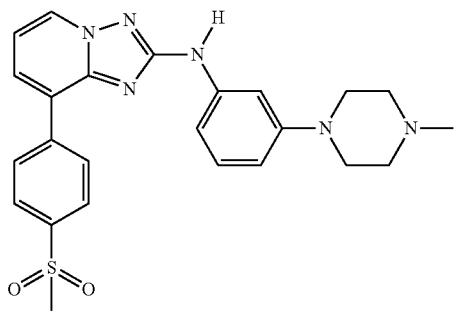 [SMILES: CN1CCN(c2cccc(Nc3nc4c(-c5ccc(S(C)(=O)=O)cc5)cccn4n3)c2)CC1]

or a salt thereof, and its use in the treatment of diseases or disorders mediated by JAK2 (Janus Kinase 2). In particular, Compound A is a potent, orally active, small molecule inhibitor of JAK2 useful for the treatment of disorders or diseases characterized by chronic systemic inflammation, such as rheumatoid arthritis (RA).

BACKGROUND

Rheumatoid arthritis (RA) is a chronic systemic inflammatory disorder that primarily affects the synovial joints. RA can also produce diffuse inflammation in the lungs and pleura as well as form subcutaneous nodular lesions. About 1-2% of the world's population is affected by RA and there is a gender bias associated with disease onset; women are three-times more likely to develop RA than men between the ages of 35 and 50.

Inflammation as the primary driver of pathology had previously been restricted to infectious diseases and autoimmune disorders; however, it is become more apparent that inflammation plays a larger role in multiple disease states such as obesity, coronary artery disease and cancer. While the precise cause of RA remains unclear, a greater understanding of the underlying mechanisms of the disease has facilitated the development of a number of therapies that target the mediators of inflammation. For example, such therapies include biologics, most notably, antibodies that capture or neutralize disease-driving cytokines.

It is well documented that JAK kinases play a pivotal role in cytokine receptor signaling to phosphorylate and activate signal transducer and activator of transcription (STAT) proteins. Several of these JAK-controlled cytokine receptor pathways are intimately involved in the initiation and progression of RA disease pathogenesis. Cytokines involved in chronic inflammatory processes (e.g., IL-2, IL-6, IL-12, IFNγ, and GM-CSF) are also essential to a proper functioning immune response to infectious agents. JAK2 is involved in the downstream activation of STAT3 and STAT5 and is responsible for transducing signals for several proinflammatory cytokines involved in the pathogenesis of RA including IL-6, IFNγ and IL-12. Other molecules implicated in the pathogenesis of RA include BLyS/BAFF, APRIL, p38/MAPK and the BCR protein tyrosine kinase, Syk.

Approved treatments for RA include NSAIDs, anti-metabolites such as methotrexate and leflunomide, various corticosteroids and glucocorticoids, sulfasalazine, and various biologics including abatacept (Orencia®), adalimumab (Humira®), etanercept (Enbrel®), infliximab (Remicade®), golimumab (Simponi®), and rituximab (Rituxan®). The recent FDA approval of tocilizumab (anti-IL-6R) (Actemra®) further demonstrates the power of targeting cytokines and associated receptors to treat chronic inflammatory diseases.

However, biologics present several disadvantages over orally active small molecules, such as the cost of production, the need for multiple injections, and the possibility for anaphylactic reactions. Small molecules are thought to provide another, perhaps complimentary, approach to treating inflammation by targeting cytokine pathways via the inhibition of key kinases involved in transducing cytokine receptor signals. Oral bioavailability is another reason that small molecules are an attractive method to treat disease.

Therapeutic control of chronic inflammation is essential for the clinical management of many highly prevalent disease states including RA. Accordingly, the development of safe and effective treatments for these debilitating conditions remains an important medical need.

BRIEF DESCRIPTION OF THE FIGURES

FIG. 1A: Depicts the enzymatic inhibitory activity of Compound A against JAK2 and other selected kinases.

Inhibition of the kinase activity of each recombinant enzyme (JAK2, JAK3) by Compound A was evaluated in a plate-based TRF detection system. The effect of Compound A in a cellular system was measured using irf-bla TF-1 cells (JAK2) and Ba/F3 (JAK3) cells. These cells were not tested for the presence of JAK1 and TYK2. $IC_{50}$ values are reported as the average±standard deviation of at least 4 independent determinations.

Figure 1B:
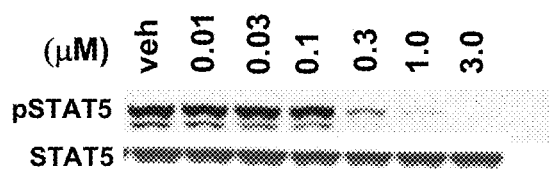
FIGS. 1A through 1C: Biochemical and cellular characterization of Compound A

FIG. 1B: Depicts the in vitro activity of Compound A in HEL92 cells as determined by the inhibition of phosphorylation of STAT5.

HEL92 cells were treated with increasing concentrations of Compound A, as indicated, for 1 hour in a serum-free media. Extracts were prepared in a Triton-based lysis buffer, protein concentrations were determined and equal amounts were resolved on SDS-PAGE gels and blotted. STAT5 and pSTAT5 were analyzed using specific antibodies. Blots were scanned and signal for each group was determined using GelPro® as phosphor/total. Prism® software was used to calculate the $IC_{50}$ values.

Figure 1C:
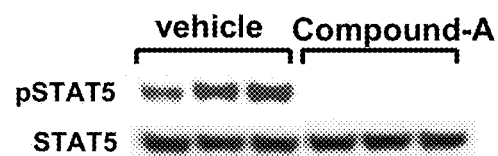

FIG. 1C: Depicts the results of an in vivo PD (pharmacodynamic) assay in which mice were dosed p.o. (per os; by mouth) with 55 mg/kg of Compound A before the removal of HEL92 tumor extracts (2 hours post injection). Levels of STAT5 and pSTAT5 were quantitated via western blot. Each lane represents an individual sample.

Figures 1, 2A:
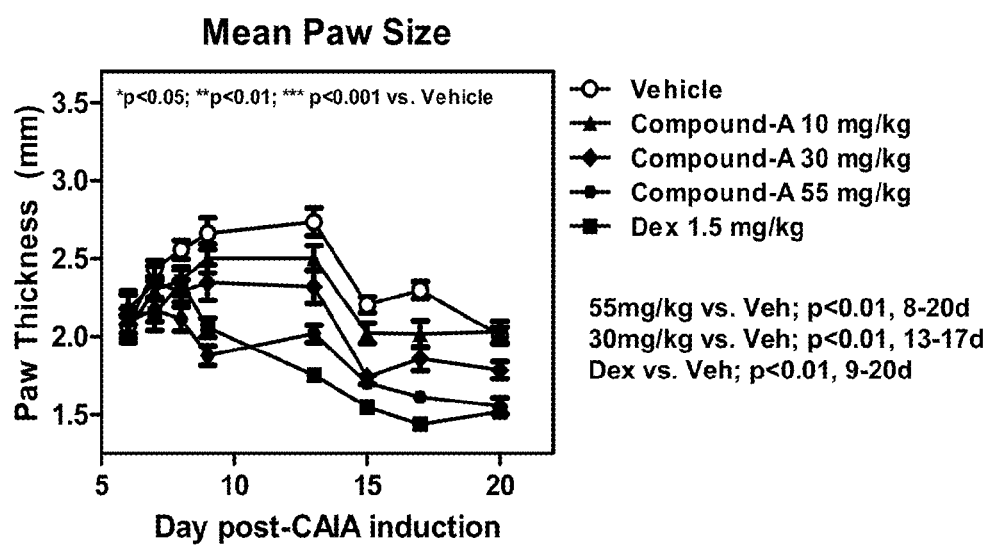
Figures 2, 2A:
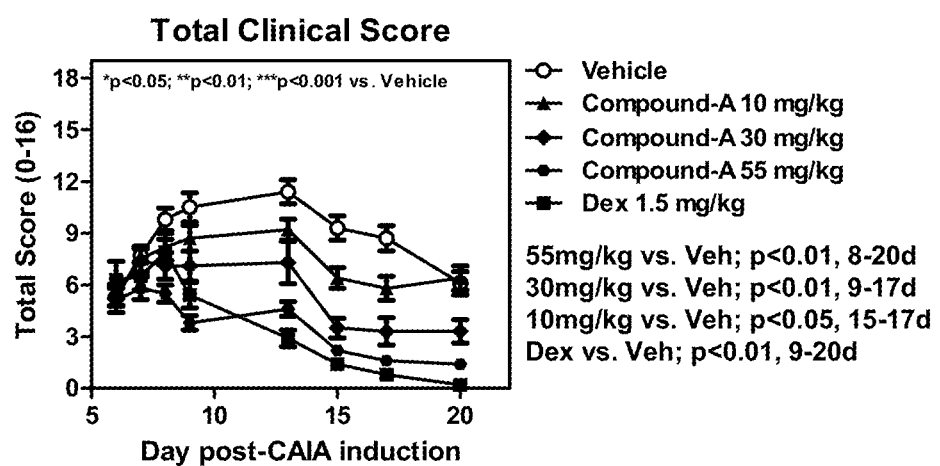
Figure 2B:
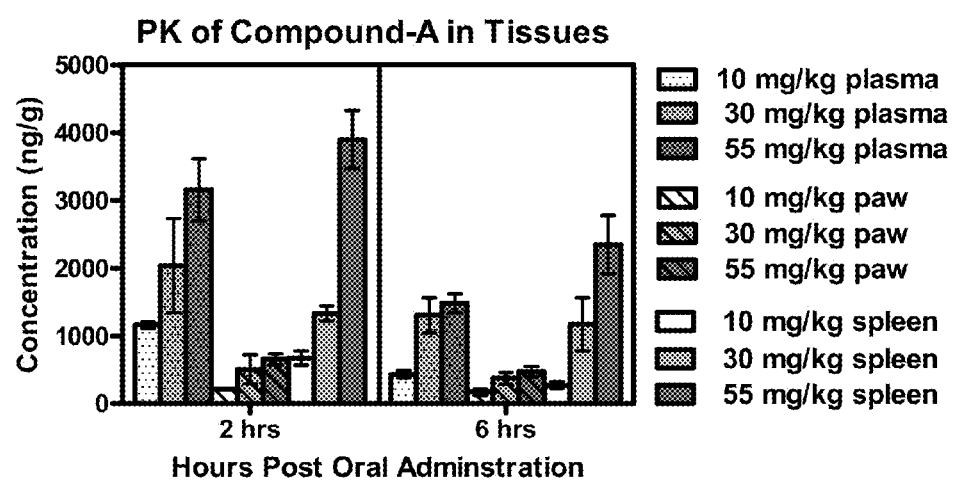

FIGS. 2A through 2B: Depicts the results of JAK2 inhibition on collagen-antibody-induced-arthritis (CAIA) paw inflammation Female DBA/1 mice were injected i.v. (intravenous) with purified anti-collagen type II antibodies, then given 25 μg of LPS (lipopolysaccharide), i.p. (intraperitoneal), three days later to induce arthritis by day 5. Mice that met the arthritis criteria score of 1 per paw were entered into the study. Compound A was administered orally, b.i.d. (twice daily), for all doses tested; Dex (Dexamethasone) was administered at 1.5 mg/kg three times a week, i.p.; and vehicle (PEG400+1% DMSO) was administered orally.

FIG. 2A-1: Depicts mean paw size (individual paws measured for thickness) measured over time.

FIG. 2A-2: Depicts total clinical score from each paw. The data in the figure represents a 2-way ANOVA analysis, N≥10 mice per group.

FIG. 2B: Depicts the results of a PK (pharmacokinetic) study of Compound A, 55 mg/kg, 30 mg/kg and 10 mg/kg, p.o., s.i.d. (once daily), in the plasma, paw and spleen of treated mice, N=3 mice per group tested. The data shown in the figure represents the mean±SEM (standard error of the mean).

FIGS. 3A through 3E: Depict the effects of treatment in a CAIA model.

DBA/1 female mice were injected i.v. with purified anti-collagen type II antibodies, then given 25 μg of LPS i.p. three days later to induce arthritis by day 5. Mice that met the arthritis criteria score of 1 per paw were entered into the study. Compound A was provided orally, b.i.d., for all doses tested; Dex was provided at 1.5 mg/kg three times a week, i.p.; and vehicle (PEG400+1% DMSO) was provided orally.

Figure 3A:
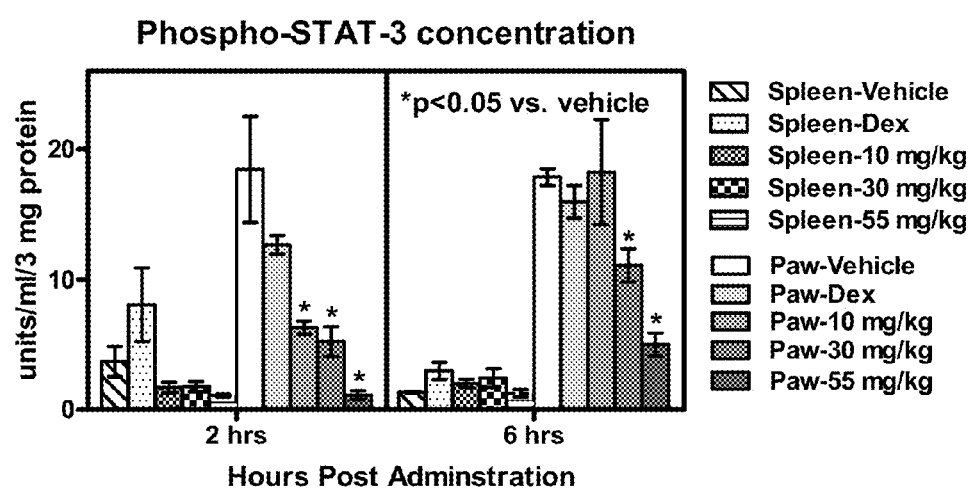

FIG. 3A: Depicts the effect of treatment on the concentration of phospho-STAT3 in the spleen and paw over time. The graphed data was generated using Luminex® bead kits, concentration in units per ml per 3 mg of total protein as determined by the BSA assay. The graphed data represents mean±SEM, statistics were performed using 2-way ANOVA analysis.

Figure 3B:
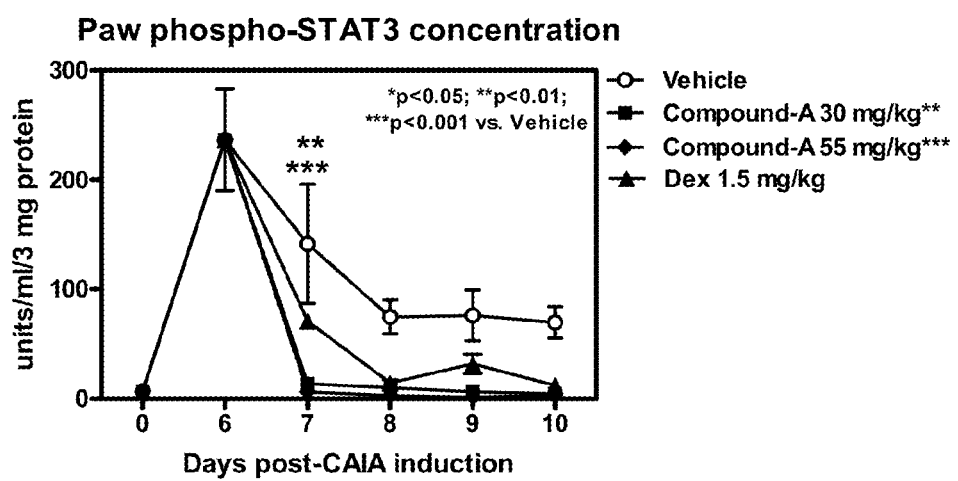
Figures 1, 3C:
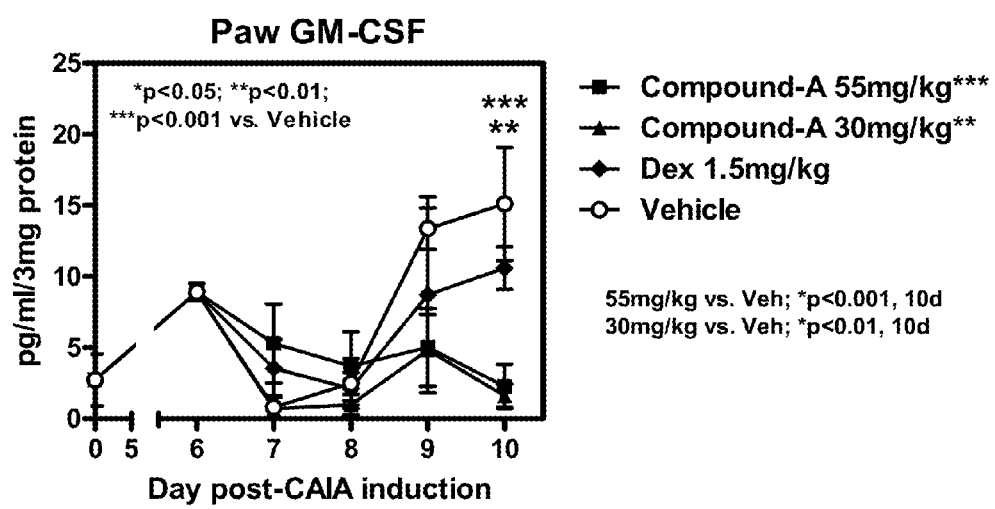
Figures 2, 3C:
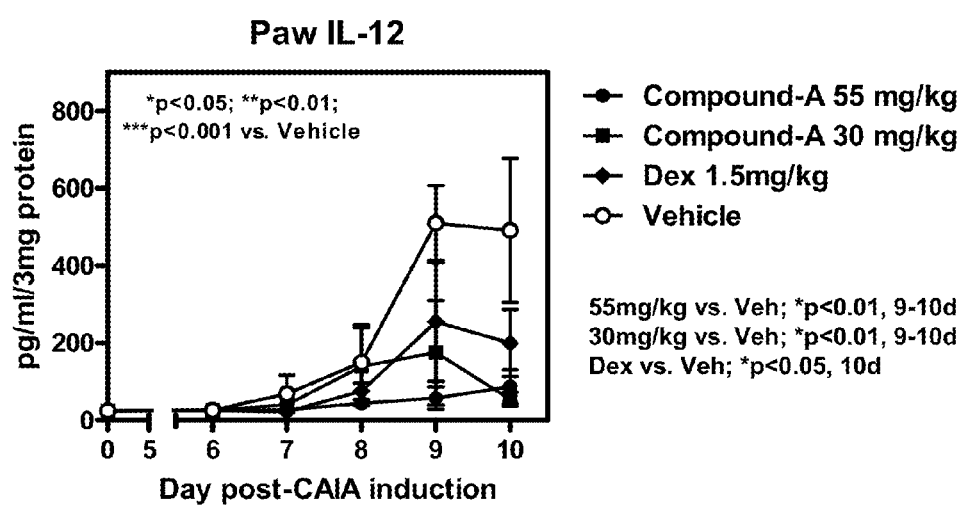
Figures 3, 3C:
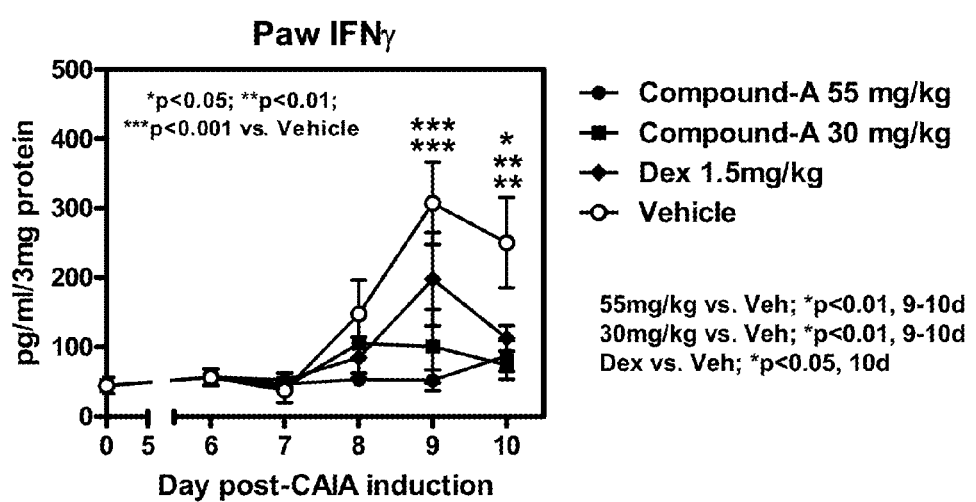

FIG. 3B: Depicts the effects of treatment on phospho-STAT3 concentration in arthritic (CAIA) paws.

FIGS. 3C-1 through 3C-6: Depict the effects of treatment on various cytokines (IL-12, IFNγ, IL-2, IL-1β, TNFα and GM-CSF) in arthritic (CAIA) paws. The cytokines were measured using known procedures [32].

FIG. 3D: Images of H&E (Hematoxylin and Eosin) stained paraffin wax-embedded sections of the carpus and tarsus from all treatment groups. Representative tissue images are shown at 10×. Tissues were also stained with Safranin-O to evaluate matrix degeneration. Five representative mice from each group were sent for histological analysis and graded according to a scoring method described herein. The data in the figures represent mean±SEM, all statistics were performed using Prism® software and 2-way ANOVA analysis.

Figures 3, 3C, 4:
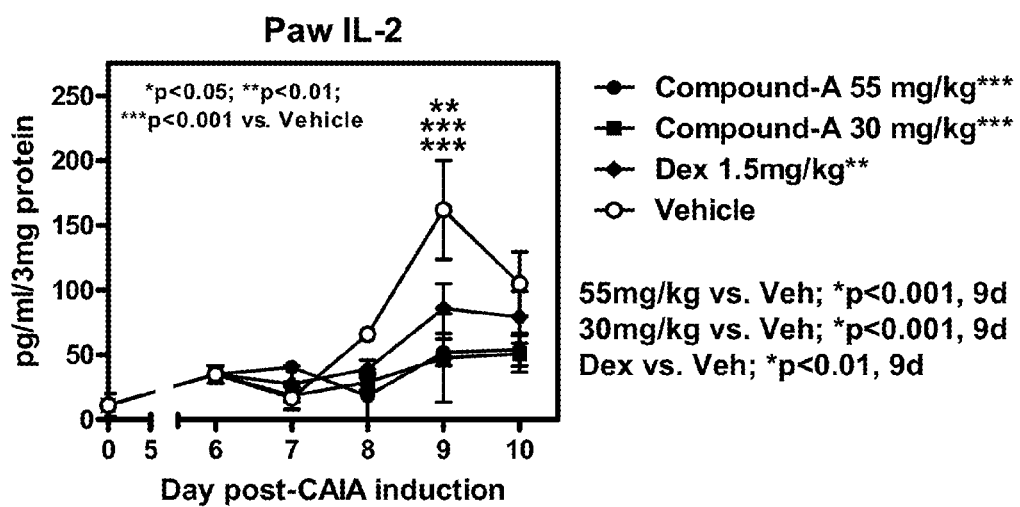
Figures 3, 3C, 4, 5:
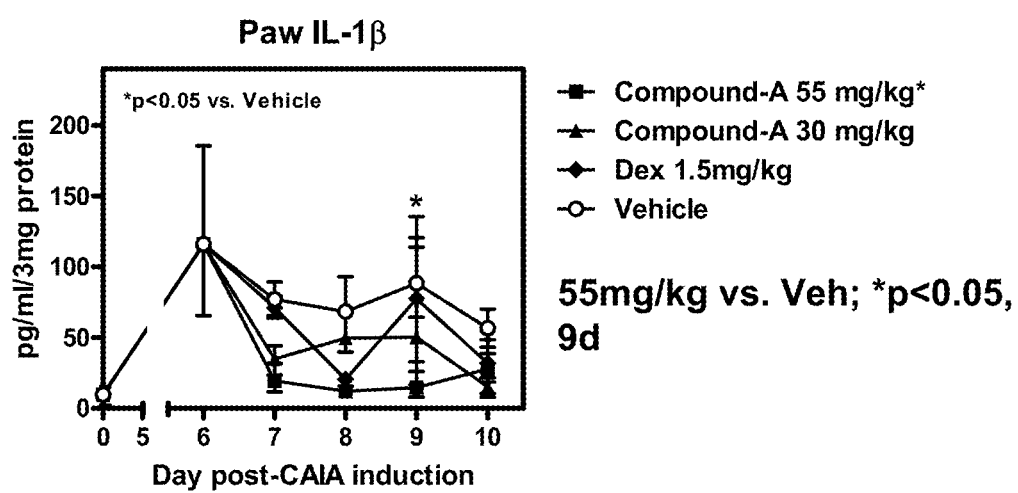
Figures 3, 3C, 4, 5, 6:
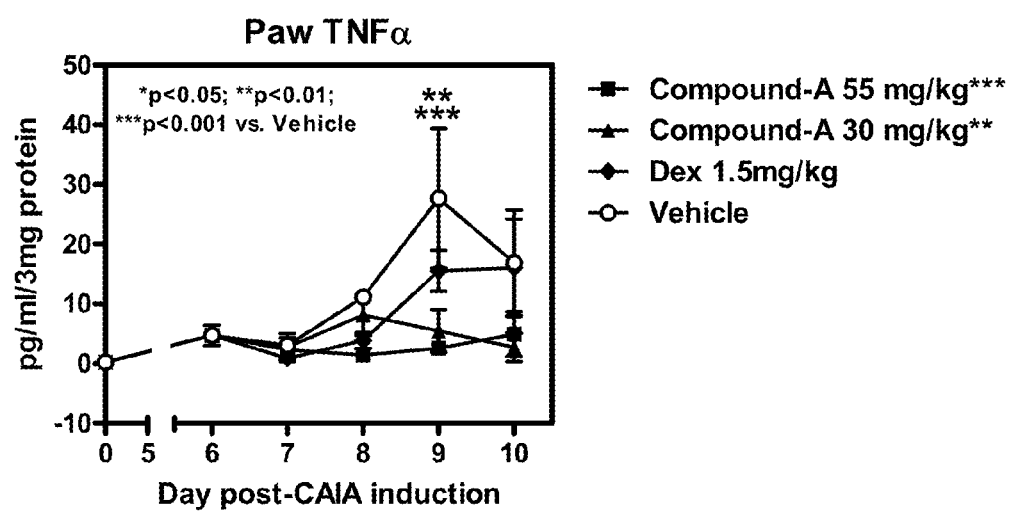
Figure 3E:
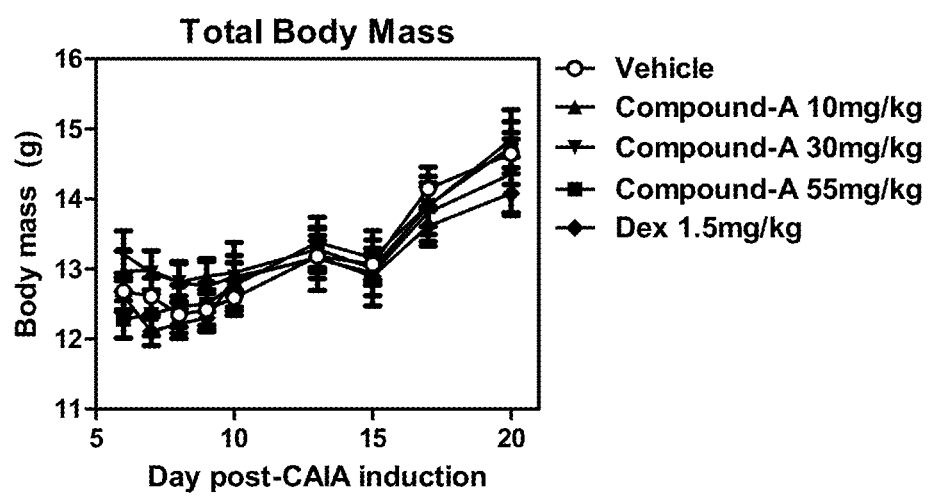

FIG. 3E: Depicts the effect of treatment on total body mass in a CAIA model

FIGS. 4A through 4E: Depict the results of JAK2 inhibition in a collagen-induced arthritis (CIA) model.

Female DBA/1 mice were injected with purified collagen type II in CFA i.d. (intradermal), then boosted with collagen type II in IFA, s.c., (subcutaneous) on day 21 followed by a day 28 LPS injection i.p. to induce arthritis (CIA). Mice that scored a '1' or better for each paw were considered arthritic and entered into the study. Treatments started after 7-10 days of arthritis induction. Compound A was provided orally, b.i.d., for all doses tested; Dex was administered i.p. at 1.5 mg/kg, three times a week; and vehicle (PEG400+1% DMSO) was provided orally, b.i.d.

Figures 1, 4A:
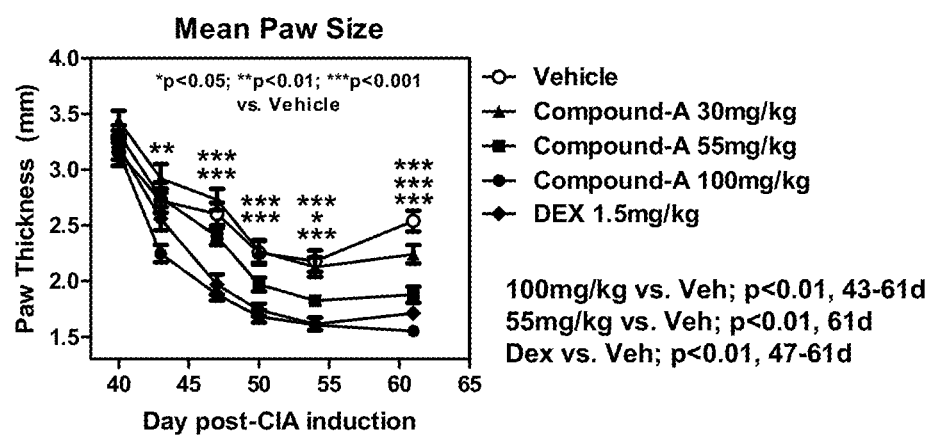
Figures 2, 4A:
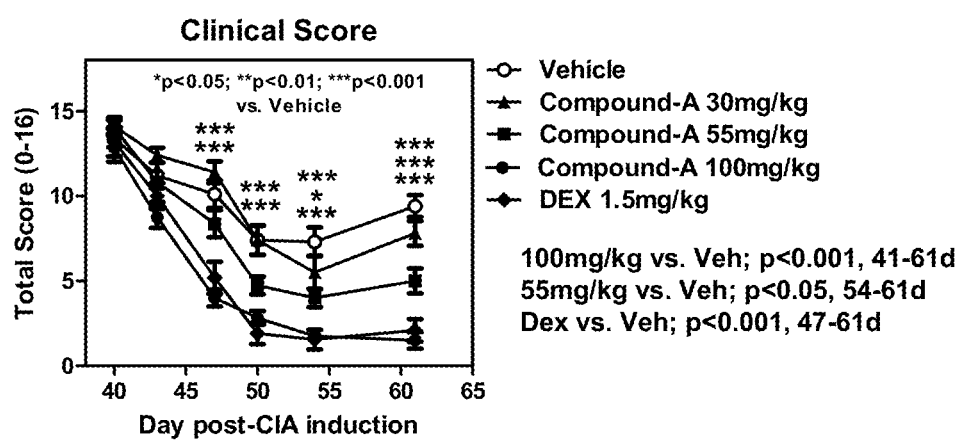

FIGS. 4A-1 and 4A-2: Depict the effects of treatment on mean paw size (individual paws measured) and the respective clinical scores for each treatment group.

Figure 4B:
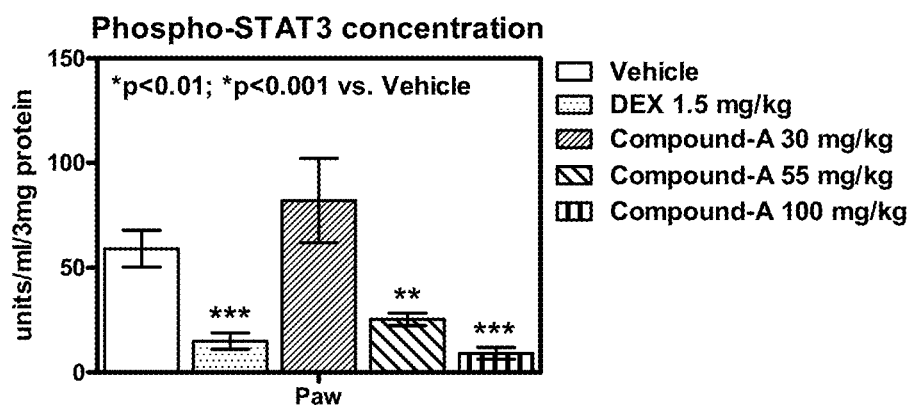

FIG. 4B: Depicts Phospho-STAT3 expression in arthritic paws for each treatment group.

Figures 1, 4C:
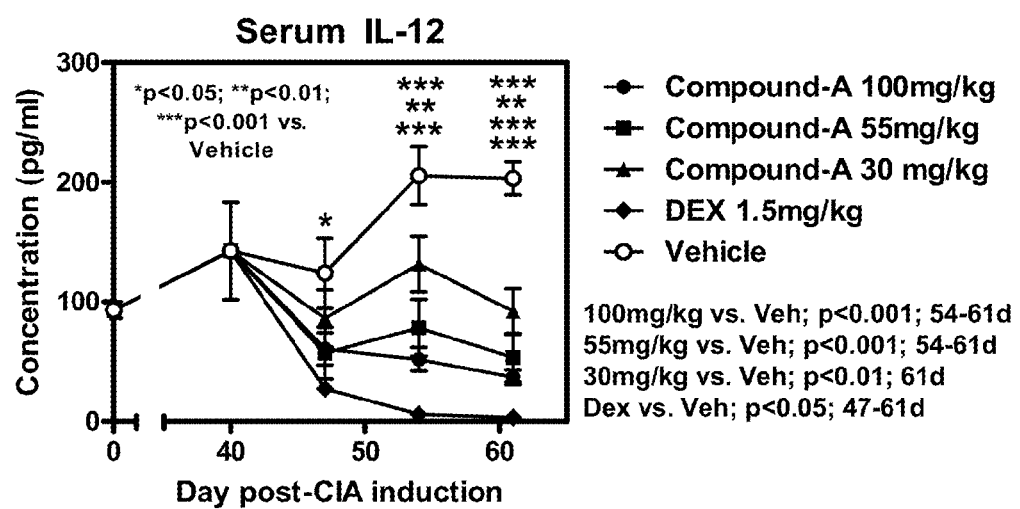
Figures 2, 4C:
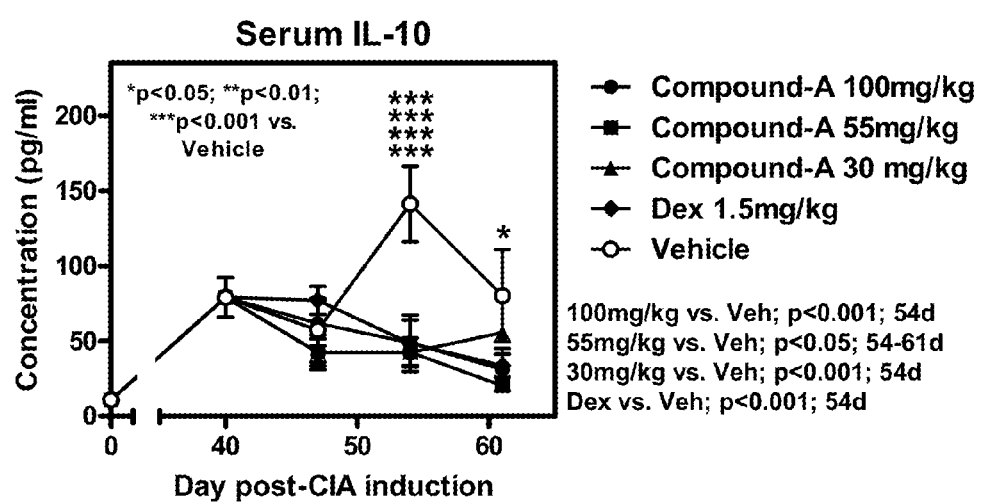
Figures 3, 4C:
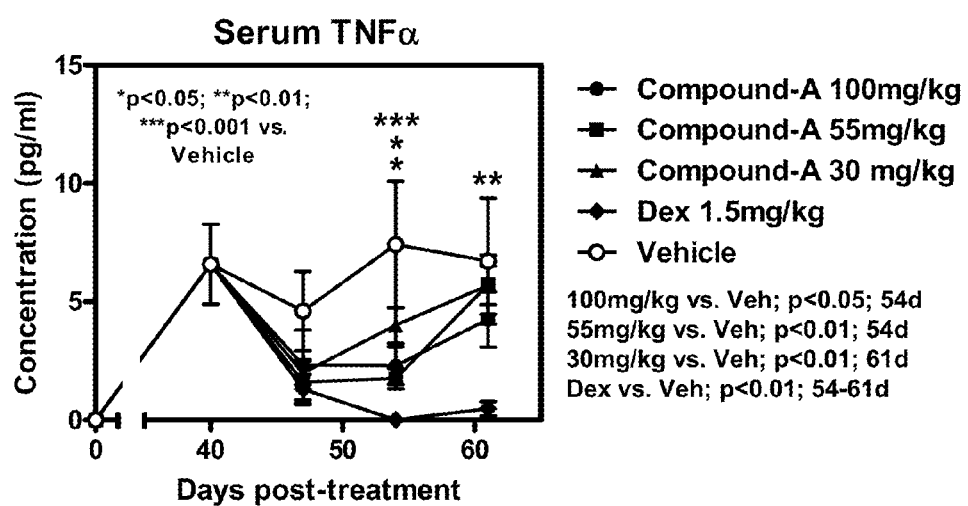
Figures 4, 4C:
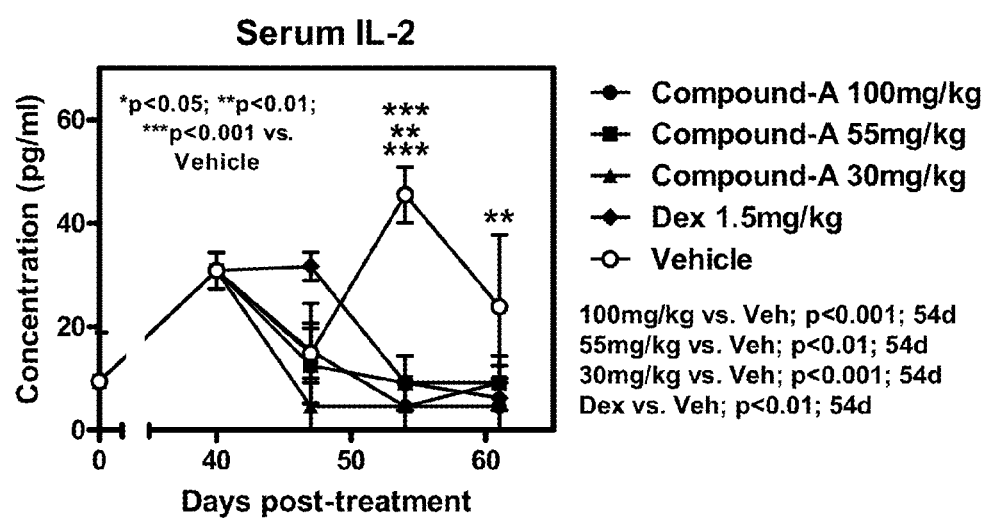

FIGS. 4C-1 through 4C-4: Depict concentrations of various serum cytokines (IL-12, IL-2, IL-10 and TNFα) in arthritic paws in each treatment group.

FIG. 4D: Depicts IFNγ Elispot® results from stimulated splenocytes from treated mice challenged with collagen type II fragment (CB11), OVA or media alone. The Elispot images shown in the figure are representative of each treatment group and the bar graph represents data using four mice from each treatment group. Spots were counted using a C.T.L. Immunospot Elispot scanner and spot counting software.

Figure 4E:
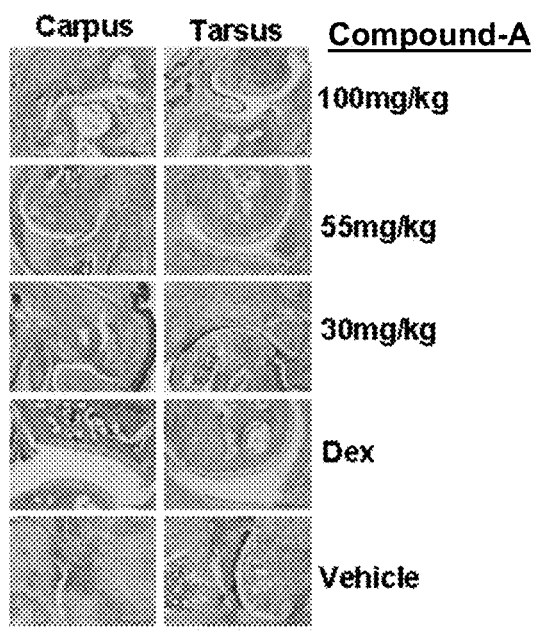

FIG. 4E: Images of H&E stained paraffin wax embedded sections of the carpus and tarsus from all treatment groups. Representative images are shown at 10×. Tissues were also stained with Safranin-O to detect matrix degeneration and this information was used for scoring. The data in the figure represents mean±SEM, statistics were performed using Prism® software and 2-way ANOVA analysis, *p<0.05, p<0.01, *p<0.001.

Figure 5A:
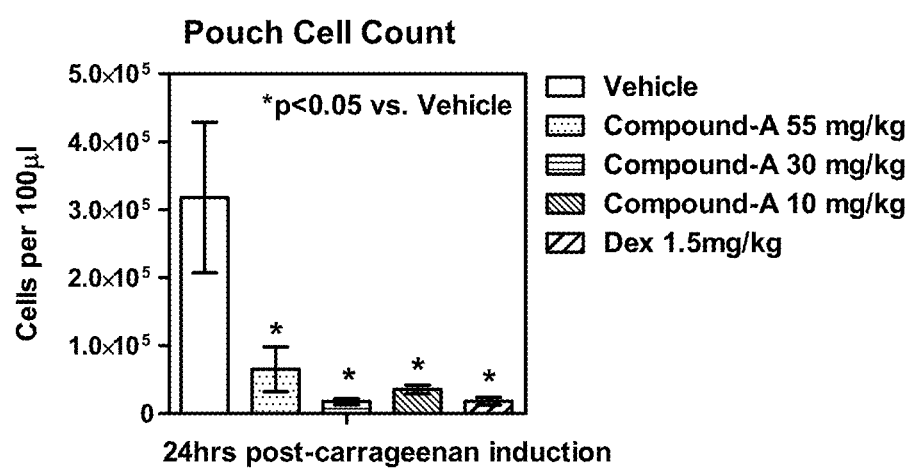
Figure 5B:
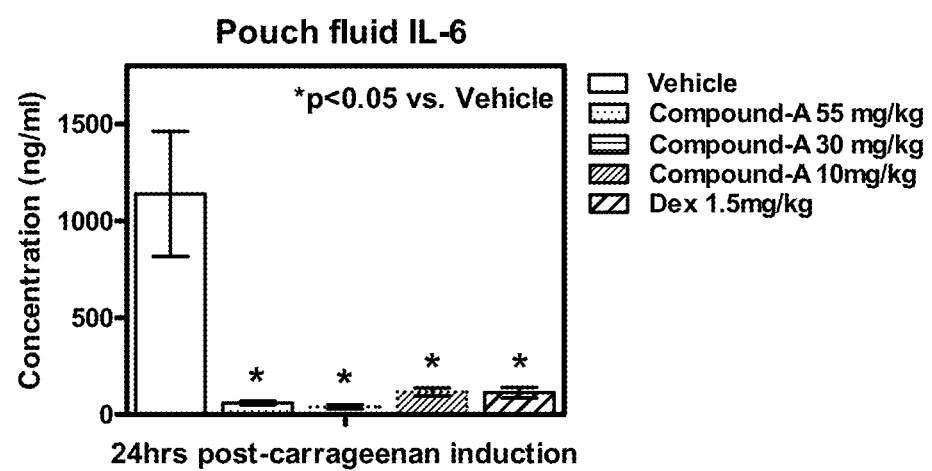
Figure 5C:
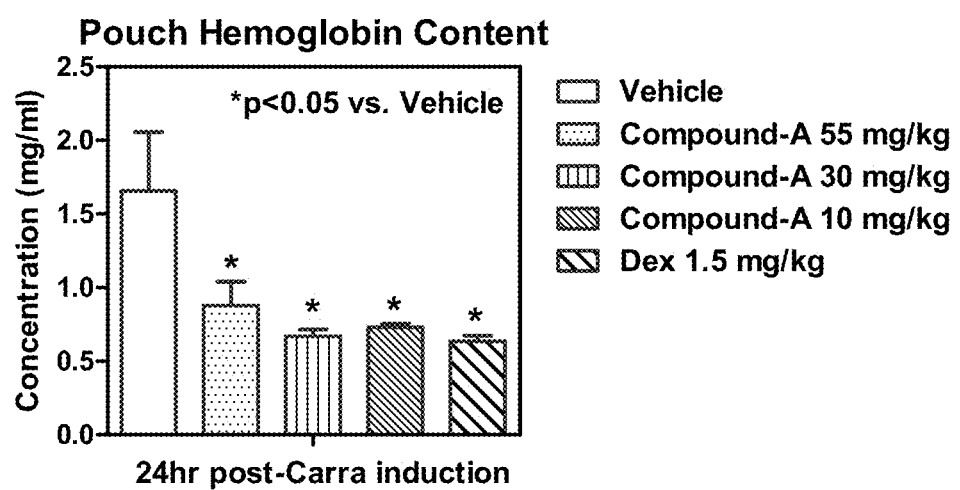

FIGS. 5A through 5C: Depicts the effects of treatment on Carrageenan-induced Inflammation Balb/c mice were induced for air pouch initiation (see materials and methods) using sterile air. Carrageenan at 1% in saline was injected directly into the pouch followed by treatment with Compound A or dexamethasone (Dex) 1 hour later. One-hundred microliters of air pouch fluid was removed 24 hours post-administration.

FIG. 5A: Depicts total cell count using 7-AAD exclusion via flow cytometeric analysis and BD TruCount beads.

FIG. 5B: Depicts fluid supernatant IL-6 concentration as determined by Luminex® cytokine analysis.

FIG. 5C: Depicts hemoglobin content as assessed by the Drabkin's assay. All data shown in the figures represent mean±SEM, and statistics were performed using 2-way ANOVA analysis, *p<0.05, N=5 mice per group tested.

FIG. 6: CAIA Model Joint Inflammation Histopathology Scores (Table I)

H&E and Safranin-O stained paraffin wax embedded carpus and tarsus sections were scored by a board certified, independent pathologist for the criteria described in the materials and methods. Tabulated data represent mean±SD (standard deviation) values for the tarsus only. Statistics were performed using 2-way ANOVA analysis, *p<0.05; p<0.01; *p<0.001, N=5 mice per group tested.

FIG. 7: CIA Model Joint Inflammation Histopathology Scores (Table II)

H&E and safranin-O stained paraffin wax embedded carpus and tarsus sections were scored by a board certified, independent pathologist for the criteria described in the materials and methods. Tabulated data represent mean±SD values for the tarsus only. Statistics were performed using 2-way ANOVA analysis, *p<0.05; p<0.01; *p<0.001, N=5 mice per group tested.

Figure 8A:
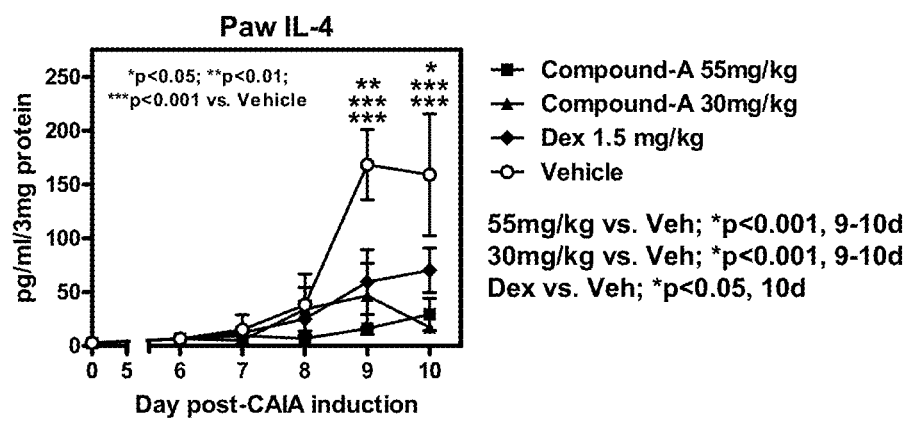
Figure 8B:
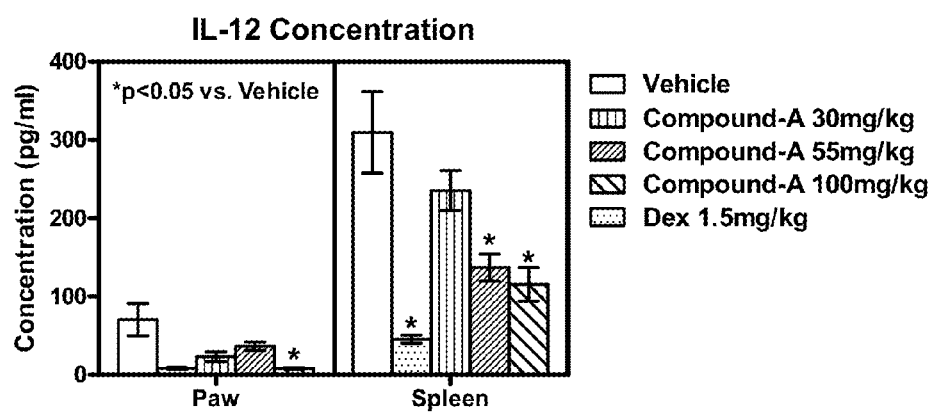
Figure 8C:
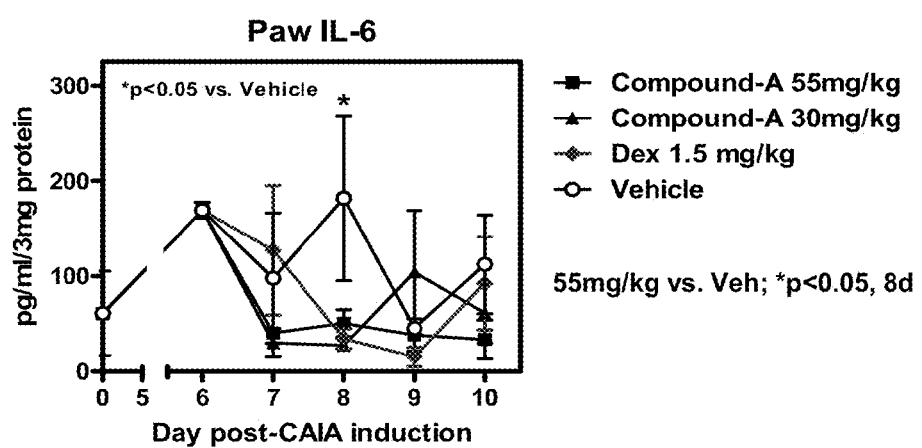

FIGS. 8A through 8C: Depict the effect of treatment in a CAIA model

Female DBA/1 mice were injected with purified collagen type II in CFA i.d. then boosted with collagen type II in IFA, s.c., on day 21 followed by a day 28 LPS injection, i.p., to induce arthritis (CIA). Mice that scored a '1' or better for each paw were considered arthritic and entered into the study, treatments started after several days of full arthritis. Compound A was provided orally, b.i.d., for all doses tested; Dex was provided, i.p., at 1.5 mg/kg, three times a week; vehicle (PEG400+1% DMSO) was provided orally, b.i.d.

Data shown in the figure represents mean±SEM.

FIG. 8A: Depicts the effects of treatment on paw IL-4 concentration, 4 hours post dosing.

FIG. 8B: Depicts the effects of treatment on cytokine IL-12 concentration, 4 hours post dosing.

FIG. 8C: Depicts the effects of treatment on paw IL-6 concentration, 4 hours post dosing.

Figure 9A:
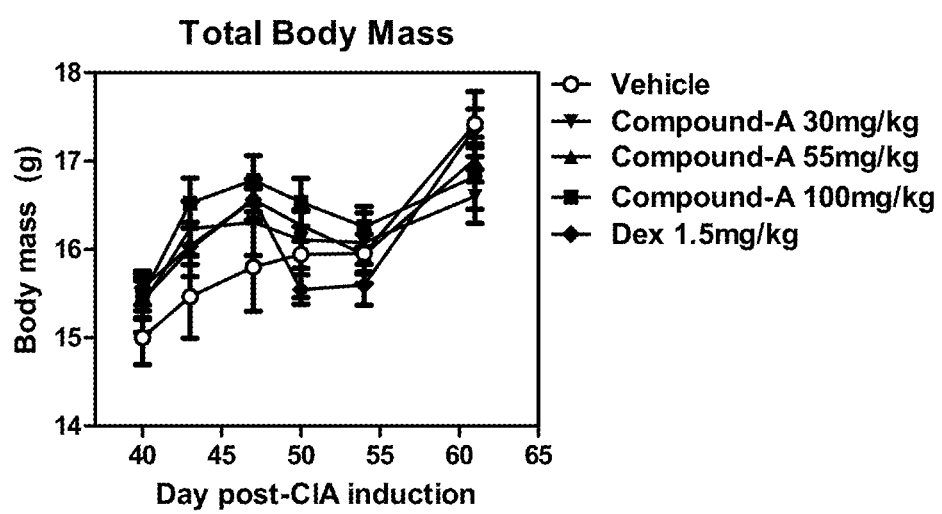
Figure 9B:
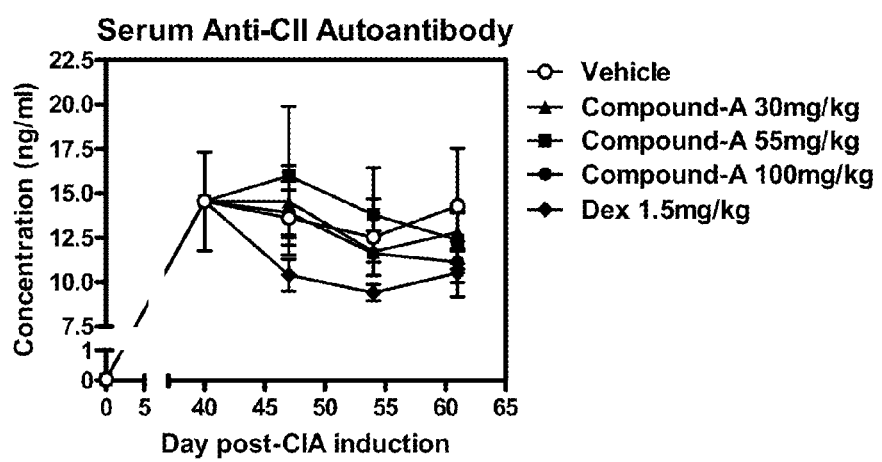

FIGS. 9A and 9B: Depict the effect of treatment on body mass and serum anti-CII autoantibody concentration in a CIA model.

Female DBA/1 mice were injected with purified collagen type II in CFA i.d. (intradermal) then boosted with collagen type II in IFA s.c. (subcutaneous) on day 21 followed by a day 28 LPS injection i.p. (intraperitoneal) to induce arthritis (CIA). Mice that scored a '1' or better for each paw were considered arthritic and entered into the study, treatments started after several days of full arthritis. Compound A was provided orally, b.i.d., for each dose tested; Dex was provided i.p. at 1.5 mg/kg three times a week; vehicle (PEG400+1% DMSO) was provided orally, b.i.d.

Serum was collected at weekly intervals and stored at −80° C. until tested. Anti-collagen type II autoantibody ELISA was performed as described in the materials and methods according to known procedures [18]. Data shown in the figures represents mean±SEM; statistics were performed using 2-way ANOVA analysis, N≥10 mice per group tested.

DETAILED DESCRIPTION

The following provides additional non-limiting details of the methods of treating chronic systemic inflammatory disorders and diseases, such as rheumatoid arthritis (RA), by inhibition or modulation of the activity of JAK2. The following also provides non-limiting details of particular compounds, such as Compound A, that inhibit or modulate the activity of JAK2, and methods of using these compounds for the treatment of diseases or disorders characterized by chronic systemic inflammation such as rheumatoid arthritis. The section titles used herein are for indexing and search purposes only and should not be construed as limiting in any way.

In one aspect, this application describes and provides a method of treating rheumatoid arthritis, the method comprising the steps of: identifying an individual affected by rheumatoid arthritis or an individual susceptible to the development of rheumatoid arthritis, and administering to said individual a therapeutically effective amount of a JAK2 inhibitor having the formula:

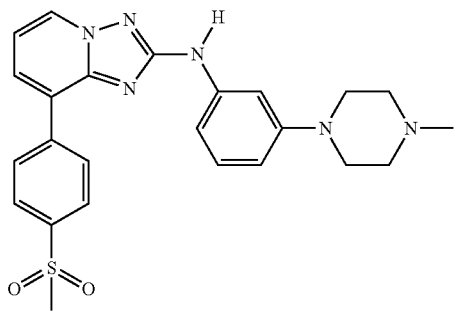 [SMILES: CN1CCN(c2cccc(Nc3nc4c(-c5ccc(S(C)(=O)=O)cc5)cccn4n3)c2)CC1]

or a salt thereof.

In another aspect, this application describes and provides a method of treating chronic systemic inflammation, the method comprising the steps of: identifying an individual affected by chronic systemic inflammation, and administering to said individual a therapeutically effective amount of a JAK2 inhibitor having the formula:

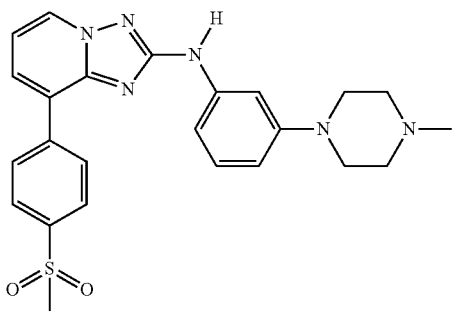 [SMILES: CN1CCN(c2cccc(Nc3nc4c(-c5ccc(S(C)(=O)=O)cc5)cccn4n3)c2)CC1]

or a salt thereof.

In another aspect, this application describes and provides a method for reducing at least one symptom of chronic inflammation in a subject, the method comprising the steps of administering a JAK2 inhibitor having the following formula:

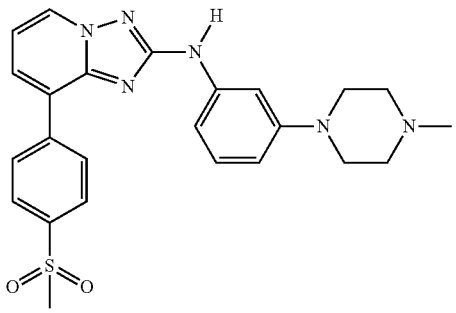 [SMILES: CN1CCN(c2cccc(Nc3nc4c(-c5ccc(S(C)(=O)=O)cc5)cccn4n3)c2)CC1]

or a salt thereof, in an amount effective to inhibit JAK2 kinase.

In another aspect, this application describes and provides a method according to any of those described above, where the JAK2 kinase inhibitor is administered up to four times per day.

In another aspect, this application describes and provides a method according to any of those described above, where the JAK2 kinase inhibitor is administered in an amount between about 0.01 mg/kg to about 1500 mg/kg per day.

In another aspect, this application describes and provides a method according to any of those described above, where the JAK2 inhibitor is administered in combination with at least one additional therapeutic agent.

In another aspect, this application describes and provides a method according to any of those described above, where the JAK2 inhibitor and at least one additional therapeutic agent are administered separately.

In another aspect, this application describes and provides a method according to any of those described above, where the JAK2 inhibitor and at least one additional therapeutic agent are administered together as a single, fixed dose combination.

In another aspect, this application describes and provides a composition for treating chronic systemic inflammation comprising a compound having the following formula:

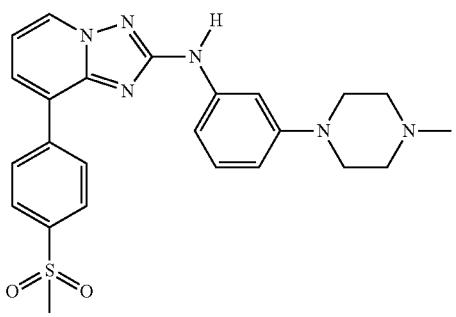 [SMILES: CN1CCN(c2cccc(Nc3nc4c(-c5ccc(S(C)(=O)=O)cc5)cccn4n3)c2)CC1]

or a salt thereof, in an amount effective for reducing the symptoms of chronic inflammation in a mammalian subject, and at least one pharmaceutically acceptable excipient.

In another aspect, this application describes and provides a composition for treating chronic inflammation comprising a therapeutically effective amount of a compound having the following formula:

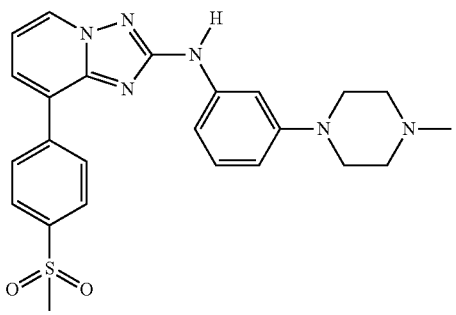 [SMILES: CN1CCN(c2cccc(Nc3nc4c(-c5ccc(S(C)(=O)=O)cc5)cccn4n3)c2)CC1]

or a salt thereof, in admixture with at least one pharmaceutically acceptable excipient and, optionally, at least one additional therapeutic agent.

In another aspect, this application describes and provides a composition according to any of those described above, where the composition is in a unit dosage form and the compound is present in an amount between about 0.01 mg/kg to about 1500 mg/kg.

In another aspect, this application describes and provides a composition according to any of those described above, where the composition is in unit dosage form and is in the form of a tablet or capsule.

In another aspect, this application describes and provides a composition according to any of those described above, where the composition is administered orally.

Definitions

The compounds described herein may be named according to either the IUPAC (International Union for Pure and Applied Chemistry) or CAS (Chemical Abstracts Service) nomenclature systems. It should be understood that unless expressly stated to the contrary, the terms "compound having the following formula", "Compound A" and "compound(s)" refer to and include the compound designated as Compound A and any and all salts of Compound A.

As used herein, whether by itself or in conjunction with another term or terms, it should be understood that the phrases "method of treating" and "method of treatment" may be used interchangeably with the phrase "for use in the treatment of" a particular disease. The latter phraseology was recently affirmed by the EPO as the proper format for claiming medical/therapeutic use(s) of compounds while at the same time eliminating Swiss-style format.

As used herein, whether by itself or in conjunction with another term or terms, "pharmaceutically acceptable" indicates that the designated entity such as, for example, e.g., a pharmaceutically acceptable excipient is generally chemically and/or physically compatible with other ingredients in a formulation or composition, and/or is generally physiologically compatible with the recipient thereof.

As used herein, whether by themselves or in conjunction with another term or terms, "subject(s)" and "patient(s)", refer to mammals, including humans. The term human(s) refers to and includes, a human child, adolescent or adult.

As used herein, whether by themselves or in conjunction with another term or terms, "treats", "treating", "treated", and "treatment", refer to and include prophylactic, ameliorative, palliative, and curative uses and results, or any combination thereof. It should be understood that "prophylaxis" or a prophylactic use or result do not refer to nor require absolute or total prevention (i.e., a 100% preventative or protective use or result). As used herein, prophylaxis or a prophylactic use or result refer to uses and results in which administration of a compound or composition diminishes or reduces the severity of a particular condition, symptom, disorder, or disease described herein; diminishes or reduces the likelihood of experiencing a particular condition, symptom, disorder, or disease described herein; or delays the onset or relapse (reoccurrence) of a particular condition, symptom, disorder, or disease described herein; or any combination of the foregoing.

As used herein, whether used alone or in conjunction with another term or terms, "therapeutic" and "therapeutically effective amount", refer to an amount of a compound or composition that (a) treats a particular condition, symptom, disorder, or disease described herein; (b) attenuates, ameliorates or eliminates one or more symptoms of a particular condition, disorder, or disease described herein; (c) delays the onset or relapse (reoccurrence) of a particular condition, symptom, disorder, or disease described herein. It should be understood that the terms "therapeutic" and "therapeutically effective" encompass any one of the aforementioned effects (a)-(c), either alone or in combination with any of the others (a)-(c).

As used herein, whether used alone or in conjunction with another term or terms, "therapeutic agent" refers to any substance included in a composition that is useful in the treatment of a disease, condition, or disorder or comorbidity (i.e., a disease, condition or disorder that exists simultaneously with another disease, condition or disorder) and is not Compound A.

Preparations

The pharmaceutically acceptable salts of the compounds described herein include pharmaceutically acceptable acid addition salts, metal salts, ammonium salts, organic amine addition salts, and amino acid addition salts. Examples of acid addition salts include inorganic acid addition salts such as, for example, chloride (HCl), sulfate and phosphate salts, and organic acid addition salts such as, for example, acetate, maleate, fumarate, tartrate, citrate and lactate salts. Examples of metal salts include alkali metal salts such as, for example, lithium, sodium and potassium salts, and alkaline earth metal salts such as, for example, magnesium, calcium, aluminum, and zinc salts. Examples of ammonium salts include salts such as, for example, ammonium and tetramethylammonium salts. Examples of organic amine addition salts include salts such as, for example, morpholine and piperidine salts.

Examples of amino acid addition salts include salts such as, for example, glycine, phenylalanine, glutamic acid and lysine salts.

Compound A can be formulated into a pharmaceutical composition (or simply "composition(s)" or "formulation(s)") by admixture with one or more pharmaceutically acceptable excipients. As used herein, the terms "excipient" and "excipients" refer to and include any ingredient, other than Compound A and any other therapeutic agents, as defined herein, which may be present in a composition. Accordingly, pharmaceutically acceptable excipient(s) refer to and include ingredients such as, for example, surfactants, wetting agents, flavorings/taste masking agents, vehicles, carriers, diluents, preservatives, bulking agents, solubilizing agents, and the like. The choice of excipient(s) will largely depend on factors such as, for example, the particular mode of administration, as well as the desired solubility and stability profiles, as well as the nature of the dosage form.

Compositions comprising Compound A can be prepared for any number of different modes of administration, such as, for example, parenterally, particularly in the form of liquid solutions or suspensions; orally, particularly in the form of tablets, capsules or syrups/liquids; intranasally, particularly in the form of powders, nasal drops, or aerosols; or dermally, particularly in the form of gels, creams, lotions, or trans-dermal patches. Compositions comprising Compound A can be conveniently administered in unit dosage form and may be prepared by any of the methods well known in the pharmaceutical art, for example, as described in Remington's Pharmaceutical Sciences (Mack Pub. Co., Easton, Pa., 1980).

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains between about 0.01 mg to about 1000 mg of Compound A.

Granules can be prepared using excipients such as lactose and sucrose, disintegrating agents such as starch, binders such as gelatin, and the like in a conventional manner. Powders can be prepared using excipients such as lactose and mannitol, and the like in a conventional manner. Capsules can be prepared using gelatin, water, sucrose, gum arabic, sorbitol, glycerin, crystalline cellulose, magnesium stearate, talc, and the like in a conventional manner. The capsules may contain solid particles such as beads or, alternatively, be liquid or gel filled. It is preferred that each capsule contains between about 0.01 mg to about 1000 mg of Compound A.

Syrup preparations comprising Compound A can be prepared using sugars such as sucrose, water, ethanol, and the like in a conventional manner.

Ointments comprising Compound A can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injectable preparations comprising Compound A can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic ester and chlorobutanol, antioxidants such as ascorbic acid and sodium pyrosulfite, and the like in a conventional manner.

Formulations for parenteral administration may also contain polyalkylene glycols such as polyethylene glycol, hydrogenated naphthalenes and the like. In particular, biocompatible, biodegradable lactide polymer, lactide/glycolide copolymer, or polyoxyethylene-polyoxypropylene copolymers may be useful excipients to control the release of the active Compound A. Other potentially useful parenteral delivery systems for Compound A include ethylene-vinyl acetate copolymer particles, osmotic pumps, implantable infusion systems, and liposomes. Other formulations for parenteral administration may also include glycocholate for buccal administration, a salicylate for rectal administration, or citric acid for vaginal administration. Formulations for inhalation administration may contain excipients such as, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for trans-dermal patches are preferably lipophilic emulsions.

Compound A or the pharmaceutically acceptable salts thereof may be administered alone, or in combination with one or more additional therapeutic agents as defined herein, in a pharmaceutical composition. An additional therapeutic agent may be used to treat one or more core symptoms and/or comorbidities associated with chronic systemic inflammation in general or rheumatoid arthritis in particular. In one aspect, Compound A is formulated (and administered) with at least one therapeutic agent as a fixed dose. In another aspect, Compound A is formulated (and administered) separately from the therapeutic agent(s).

Some examples of therapeutic agents that may be used in combination with Compound A include, but are not limited to, e.g., nonsteroidal anti-inflammatory agents/analgesics (NSAIDs), disease-modifying anti-rheumatic drugs (DMARDs) such as auranofin (Ridaura®), azathiaprine (Imuran®), gold sodium thiomalate (Aurolate®), methotrexate, or leflunomide, glucocorticoids such as betamethasone or prednisone, sulfasalazine, various biologic response modifiers such as, abatacept (Orencia®), adalimumab (Humira®), anakinra (Kineret®), etanercept (Enbrel®), infliximab (Remicade®), golimumab (Simponi®), rituximab (MabThera/Rituxan®), certolizumab (Cimzia®), or tocilizumab (RoActemra/Actemra®), various analgesics such as tramadol or acetaminophen, other small molecule inhibitors such as CP-690,550 (tasocitinib), VX-509, VX-702, BMS-582949, INCB-18424, INCB-28050, R-788 (fostamatinib disodium), AC430, SB1578, AG490, TG101209, CYT387, AZ960, XL019, SGI-1252, AT9283, CEP-701 (lestaurtinib), proteasome inhibitors such as bortezomib (Velcade) and PR-957/ONYX0914, and Carflizomib.

Compound A and the pharmaceutically acceptable salts thereof can be administered orally or non-orally, e.g., as an ointment or an injection. The concentrations of Compound A in a particular pharmaceutical composition can vary as described herein or as determined by one of skill in the art. In particular the concentration of Compound A in a particular dosage form will depend upon factors such as the total dosage to be administered, the chemical characteristics (e.g., hydrophobicity) of Compound A, the route of administration, the age, body weight and symptoms of a patient, etc. The preferred dosage range of Compound A is likely to depend on variables such as the type and extent of progression of the disease to be treated, the overall health status of the particular patient, the particular formulation (dosage form) and the excipients contained therein, as well as the route of administration.

Typical dosage ranges for Compound A are from about 1 μg/kg to about 3 g/kg of body weight per day. In one aspect, a preferred dosage range for Compound A is from about 0.01 mg/kg to about 1500 mg/kg of body weight per day. In another aspect, a preferred dosage range for Compound A is from about 0.1 mg/kg to about 300 mg/kg that may be administered once to four times per day. In yet another aspect, a preferred dose range of Compound A is about 30 mg/kg to about 100 mg/kg, administered once or twice daily, with oral administration being more preferred. In still another aspect, it is preferred that the about 30 mg/kg to about 100 mg/kg of Compound A is administered in a continuous manner, such as for example, via continuous infusion.

The skilled artisan will appreciate, based upon the description and examples provided herein, that the dosage range and dosing regimen for Compound A may be adjusted in accordance with methods well-known in the therapeutic arts. That is, one of skill in the art can readily determine the particular dose of Compound A and temporal requirements of administration needed to provide a detectable therapeutic benefit. Accordingly, it should be understood that while this application may describe and/or exemplify certain dose and administration regimens, these examples in no way limit the dose or administration regimens that may be used in practicing the methods described herein.

Materials and Methods
Compound A

Compound A, [8-(4-Methanesulfonyl-phenyl)-[1,2,4]triazolo[1,5-a]pyridin-2-yl]-[3-(4-methyl-piperazin-1-yl)-phenyl]-amine, has the following structure:

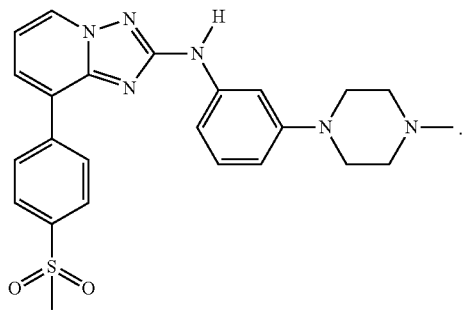 [SMILES: CN1CCN(c2cccc(Nc3nc4c(-c5ccc(S(C)(=O)=O)cc5)cccn4n3)c2)CC1]

For the experiments described herein Compound A was prepared in a manner analogous to the method described in Example 35 of International Application No. PCT/US10/37363.

The experiments and examples described herein demonstrate that Compound A is a potent, orally active JAK2 inhibitor that can ameliorate particular biological aspects and symptoms characteristic of RA. More specifically, the experiments and examples described herein demonstrate that JAK2 inhibition, as a result of the administration of Compound A, decreases several inflammatory cytokines including IL-6, IL-12, IL-13β and IFNγ both systemically and locally at the site of disease as well as treated particular symptoms of chronic, pathological joint destruction in a well-tolerated manner.

Compound A was identified as a potent inhibitor of JAK2 kinase in an assay using the isolated human enzyme ($IC_{50}$=1.8±0.6 nM, FIG. 1A). Compound A was evaluated against the other members of the JAK family and demonstrated varying degrees of selectivity from >40-fold versus JAK1 to >800-fold against TYK2 (FIG. 1A). The ability of Compound A to inhibit other members of the kinome was also assessed using binding assays for a panel of 402 kinases [25]. At a test concentration of 1 μM, Compound A was shown to be highly selective. Using the selectivity score defined by Karaman et al, 9% of the panel was inhibited by >90% and only 1% of the panel was inhibited by >99% ($S(90)_{402}$=0.09 and $S(99)_{402}$=0.01) [26]. (FIG. 1A). In an in vitro cellular system, Compound A was shown to inhibit JAK2 in HEL92 cells by measuring the phosphorylation of STAT5 (FIG. 1B). The ability of Compound A to inhibit JAK2 in vivo has been demonstrated in a pharmacodynamic (PK) assay using HEL92 cells (FIG. 1C). Other experiments utilizing the GeneBLAzer® reporter assay show that Compound A also inhibits JAK2 in irf-bla TF-1 cells.

In another experiment Compound A also exhibited some activity against pSTAT3. Studies have shown that STAT3 can be activated via the EGFR receptor and Src kinase signaling pathways [27, 28]. However, in the profiling panel mentioned above Compound A lacked activity against either of these kinases, which suggests that the effects of Compound A on pSTAT3 are mediated by the inhibition of JAK2. Taken as a whole, the in vitro and in vivo data described above is consistent with Compound A being a potent and selective inhibitor of JAK2.

The potential therapeutic benefit of JAK kinase inhibition has been demonstrated in RA with the use of CP-690,550, a potent JAK3 inhibitor originally intended for organ transplantation immunosuppression, but has since been shown to have activity against JAK1 and JAK2 as well [26]. More recently, the selective JAK1/JAK2 inhibitor, INCB028050, has demonstrated efficacy in various rodent models of RA, further demonstrating the central role JAK kinase plays in this disease [14]. The successful use of tocilizumab (Actemra®) for RA further demonstrates the mechanistic rationale of targeting cytokine pathways central to the pathogenesis of the disease and without the immunsuppressive side-effects of several of the TNFα blockade biologics [15].

JAK2 Inhibition Suppresses Collagen-Antibody-Induced Arthritis and Inhibits Local Cytokine Responses Anti-collagen type II antibody was delivered to mice i.v. and oral administration of Compound A was initiated upon meeting minimum score requirements and entry into dosage groups. Compound A was administered at 10, 30 or 55 mg/kg p.o. twice daily for two weeks total. Vehicle groups were treated with PEG400 in 1% DMSO; dexamethasone (Dex) was used as a glucocorticoid standard of care reference. Dex was given i.p. in saline alone, three times a week (every 48 hours) at 1.5 mg/kg of total body mass. This high dose of Dex was chosen to define a fully treated disease index, and is within the range (0.3-1.5 mg/kg) employed by several groups using inflammation models [29, 30, 31].

Individual paws were scored and measured using a standard electric caliper and the measurements were averaged to produce the graphed result. Dose-dependent responses were evident by the reduction in mean paw thickness or size over time with treatment (1.3-fold drop at day 13 for 55 mg/kg dose compared to vehicle) (FIG. 2A-1). These results correlated well with a decrease in total clinical score peaking at the highest dose used, 55 mg/kg, (2.4-fold reduction at day 13 for 55 mg/kg dose compared to vehicle) (FIG. 2A-2). On days 13 through 20 post-CAIA induction, the efficacy observed for 55 mg/kg dose of Compound A was similar to the results observed with Dex (FIG. 2A-2).

Analysis of the concentration of Compound A in plasma, paw and spleen at 2 and 6 hours post-administration on day 20 demonstrated dose-related increases in the levels of compound A in these tissues (FIG. 2B). While the level of Compound A in the target tissue, i.e., the paw, was relatively low, the levels of Compound A were relatively constant between the two time points for the 55 mg/kg treatment group. This result suggests that Compound A is retained in the diseased (i.e., inflamed) tissue over time and therefore may be effective in treating the symptoms of chronic inflammation and/or RA at these sites post-administration. The data (mean±SEM, N=3) represented in FIG. 2B is tabulated below:

| Dose | Plasma (2 hrs) | Plasma (6 hrs) | Paw (2 hrs) | Paw (6 hrs) | Spleen (2 hrs) | Spleen (6 hrs) |
|---|---|---|---|---|---|---|
| 10 mg/kg | 1163.33 ± 48.07 | 432.67 ± 56.67 | 213.67 ± 12.39 | 172.00 ± 48.69 | 673.00 ± 102.25 | 273.33 ± 50.42 |
| 30 mg/kg | 2040.00 ± 693.47 | 1306.67 ± 257.57 | 507.67 ± 213.39 | 376.33 ± 84.71 | 1330.00 ± 112.69 | 1170.67 ± 394.71 |
| 55 mg/kg | 3156.67 ± 456.27 | 1483.33 ± 137.76 | 659.67 ± 81.13 | 472.33 ± 74.32 | 3900.00 ± 426.65 | 2346.67 ± 433.22 |

To investigate the effect of Compound A on levels of phosphorylated STATs and cytokines in the paws of treated mice, a method was developed whereby synovial fluid and cellular joint extracts could be obtained from the paws and ankles of diseased animals for analysis using multiplex bead arrays [32]. Based on the results of in vitro and in vivo experiments with Compound A (i.e., FIG. 1A-B) it was postulated that phosphorylated STAT5 (pSTAT5), STAT3 (pSTAT3) and possibly STAT1 (pSTAT1) were reduced in the paws of treated mice. Using multiplex bead kits, it was determined that measurement of phosphorylated STATs was similar and more quantitative than using western blotting alone. Consequently, multiplex analysis was used as the primary method of measuring phosphorylated STATs for all experiments described herein.

Local paw pSTAT5 levels in diseased animals were similar to vehicle alone; however, pSTAT3 dominated as the most highly upregulated STAT molecule with disease compared to non-diseased animals and was significantly reduced in total concentration upon JAK2 inhibition (FIG. 3A); pSTAT1 was barely detectable in all samples tested. Phospho-STAT3 levels were nearly abolished in the paw 2 hours after administration of 55 mg/kg of Compound A (FIG. 3A, left graph) and only slowly began to recover at 6 hours post-administration (FIG. 3A, right graph). The expression of total paw pSTAT3 decreased during the course of disease when treated with Compound A as compared to vehicle control mice (FIG. 3B). Levels of pSTAT3 were elevated in CAIA mice due to the requirement to prime mice with 25 µg of LPS on day 3 post antibody transfer, however, disease maintenance was evident from the sustained paw inflammation and pSTAT3 activity over time in these animals (FIG. 3B). Within 24 hours post Compound A b.i.d. treatment the reduction in pSTAT3 was significantly greater than that of Dex as compared to vehicle alone (FIG. 3B, day 6-7, $p<0.01$ for 30 mg/kg and $p<0.001$ for 55 mg/kg as compared to vehicle). This reduction of pSTAT3 was reached by Dex treatment 48 hours post treatment initiation (FIG. 3B, day 6-8). Compound A reduced pSTAT3 expression to the lower limits of the assay throughout the remainder of the experiment (FIG. 3B).

The reduction in paw swelling, as shown in FIG. 2A-1, and in pSTAT3 expression, as shown in FIGS. 3A and 3B, strongly suggest that at these levels of Compound A (i.e., 30-55 mg/kg) a subsequent decrease in the expression of several cytokines controlled by STAT3 should also be observed (See FIGS. 3C-1 through 3C-6). To confirm this hypothesis, the CAIA model experiment was repeated using 30 mg/kg, 55 mg/kg and 100 mg/kg doses of Compound A and the paw extracts were analyzed for the expression level of several pro-inflammatory cytokines. Both the 55 mg/kg and 100 mg/kg doses of Compound A significantly reduced the level of several of the cytokines implicated in the pathogenesis of RA [33]. Dose-dependent reductions were observed for all cytokines tested in paw extracts, especially for GM-CSF, IL-12, IL-2, and IL-4 (See FIGS. 3C-1 through 3C-6 (55 mg only) and FIGS. 8A through 86).

For several of the cytokines tested Compound A significantly decreased cytokine expression below the levels observed in the Dex treatment group. (FIG. 3C, *$p<0.05$ compared to vehicle) and the 55 mg/kg dose of Compound A lowered and sustained cytokine suppression for the remainder of the study (FIG. 3C, IL-1β, IL-6, TNFα, IL-12, **$p<0.01$ compared to vehicle). This data shows that despite the relatively high dose of Dex used in these experiments, 1.5 mg/kg, treatment with Compound A more effectively reduces a number of important clinical parameters below the levels achieved with Dex, which suggests that Compound A is more powerful and more effective than this standard of care agent.

Histological analyses of decalcified front and hind limbs showed that treatment with Compound A also reduced several clinical features associated with progressive rheumatoid arthritis. Independent pathologist scoring and image collection determined that treatment with Compound A could significantly decrease several parameters including matrix erosions, subchondral osteolysis, osteoproliferation, synovial proliferation, pannus formation and degree of inflammation as compared to vehicle controls (See FIG. 6, Table I). Dose-dependent responses upon JAK2 inhibitor treatment, i.e., treatment with Compound A, resulted in reduced bone degradation, tissue destruction and osteoarthritis as evident from the histopathology images (FIG. 3D).

For all CAIA induced animals treated with Compound A (all doses), total body mass was not significantly different from that of vehicle-treated animals (FIG. 3E). In previous experiments, non-diseased animals show similar weight gain compared to their vehicle-treated counterparts.

Inhibiting JAK2 Slows the Progression of Chronic Collagen-Induced Arthritis and Reduces the Generation of Disease Promoting Th1 Cells Compound A was then tested in a more physiologic and progressive disease model of RA (i.e., collagen-induced arthritis (CIA) model). In this experiment arthritic mice that had been previously sensitized against self-collagen type II and were exhibiting the phenotype of natural RA were treated with Compound A. Laboratory studies demonstrated that this CIA model exhibited arthritic flares as previously reported in the literature [18]. Early model optimization studies consistently generated robust collagen-induced-arthritis phenotypes that were absent from control treated, non-diseased, animals. CIA arthritic animals were separated into groups and treated with Compound A at 30, 55 and 100 mg/kg doses b.i.d, p.o.; vehicle or the standard-of-care reference drug, Dex at 1.5 mg/kg, which were administered as described above. There was a clear reduction in the mean paw size (individual values for paws were collected) along with a reduction in clinical score in a dose-dependent manner for mice treated with Compound A (FIGS. 4A-1 and 4A-2). The most striking observation was the near identical suppression of paw swelling in mice treated with 100 mg/kg Compound A versus those treated with Dex (FIG. 4A-1). Moreover, it was observed that the 100 mg/kg treatment group had a more rapid drop in swelling as compared to the Dex treatment group (FIG. 4A-1, day 43). The faster onset of swelling reduction noted for the 100 mg/kg treatment group may be explained by differences in the mechanism of action of Compound A.

As shown in FIG. 4B, pSTAT3 was also significantly reduced in mice treated with Compound A at 55 mg/kg (FIG. 4B, $p<0.01$) and 100 mg/kg (FIG. 4B, *$p<0.001$). For all three Compound A doses, the data show that the reduction in local paw pSTAT3 expression directly corresponded with a decrease in several serum and paw cytokines involved in the disease progression of arthritis (See FIGS. 4C-1 through 4C-4; IL-12, IL-2, IL-10 and TNFα, $p<0.05$, See also, FIG. 8A, IL-4, ***$p<0.001$) and spleen IL-12 (FIG. 8B, *$p<0.05$). A reduction in paw IL-6 (FIG. 8C, *$p<0.05$) with Compound A treatment was also observed in the CAIA experiment described above. However, this cytokine (IL-6) was difficult to monitor due to the apparent IL-6-driven flares causing spikes in the vehicle groups (FIG. 86). Body mass did not significantly change for any group tested, however, mice treated with Compound A appeared healthier and retained greater body mass longer than control groups (FIG. 9A).

Dose responses of Compound A treatment was most clearly observed when IL-12, the main precursor and driver of pathogenic Th1 and Th17 cells [34, 35], was measured (FIG. 4C-1). The dose of Dex administered in this experiment (1.5 mg/kg) was effective at suppressing endogenous IL-12 expression in the serum of arthritic mice, however, all three doses of COMPOUND A were able to significantly decrease the level of IL-12 comparable to that observed with Dex (FIG. 4C-1). Since IL-12 is the differentiating cytokine for Th1 cells (via T-bet expression) and anti-collagen type II Th1 cells are one of the main drivers of paw inflammation in the CIA model, it was hypothesized that if Compound A can suppress circulating IL-12, then the total frequency of collagen-type II specific T cells should reduce upon treatment. Because the Th1 cells found locally in the paw would have circulated throughout the animal and entered secondary lymphoid organs, whole splenocytes from treated CIA mice were restimulated with the purified collagen type II fragment (CB11) containing immunodominant epitopes ex vivo in IFNγ T-cell Elispot assays. As shown in FIG. 4D, there was a significant reduction in the frequency of CB11-specific, IFNγ secreting T cells when treated with either Dex or Compound A at 55 mg/kg, or 100 mg/kg b.i.d, p.o. for four weeks (FIG. 4D, *$p<0.001$). Representative Elispot blot images demonstrate that higher doses of Compound A results in a greater reduction in the frequency of Th1-like cell responses (FIG. 4D). However, a reduction in anti-CII IgG serum titers in Compound A treated mice was not observed (FIG. 9B), suggesting that the root of the problem—autoreactive B cells still has to be addressed [36]. Anti-CII antibodies were not present in non-arthritic mice, and anti-CI antibodies were tested but were never found in this experiment or the CIA model. Disease treatment using Compound A may lead to less paw inflammation and bone deterioration as demonstrated by histological analysis (FIG. 4E) and independent, blinded, pathologist scores (FIG. 7, Table II). In the CIA model, the tarsus tends to become more inflamed than the carpus, while the opposite effect is observed in the CAIA model. Both 100 mg/kg and 55 mg/kg doses of Compound A provided protection in the tarsus; however, the 100 mg/kg dose of Compound A provided the best protection for both regions (FIG. 4E). Significance was only observed for the degree of inflammation in the CIA model for both the 100 mg/kg and 55 mg/kg Compound A doses (FIG. 7, **$p<0.01$ for 100 mg/kg and *$p<0.05$ for 55 mg/kg compared to vehicle controls).

Inhibition of Cellular Immunity with JAK2 Inhibition Using an Air Pouch Inflammation Model To test the impact of Compound A inhibition of JAK2 at the cellular level, the mouse air pouch model (APM) was utilized. Air-filled subcutaneous pouches were maintained under sterile conditions and injected with 1% carrageenan simultaneously with Compound A at 10, 30 and 55 mg/kg. Saline alone (vehicle) or dexamethasone at 1.5 mg/kg were used as controls. Compound A JAK2 inhibition significantly decreased cellular accumulation in the air pouch (FIG. 5A, *$p<0.05$ as compared to vehicle). JAK2 inhibition vis-à-vis treatment with Compound A was also shown to inhibit the expression of IL-6 to below that of Dex (FIG. 5B, *$p<0.05$ as compared to vehicle). In addition, angiogenesis was impacted as measured using the indirect angiogenesis assay, Drabkin's assay, measuring total hemoglobin content of the pouch contents (FIG. 5C, *$p<0.05$ as compared to vehicle). Air pouch model (APM) model treatment with Compound A provided similar results when administered at 1-0.1 mg/kg. These data suggest that inhibition of JAK2 by Compound A directly affects cellular immune function and thus the mechanism of action in the RA models must be mediated at the level of leukocyte flux and cytokine release/response.

Animals, Antibodies, Cell Culture Reagents, Compounds, Cell Lines

Mice used for CIA and CAIA studies were Harlan female DBA/1 mice; female Balb/c mice from Jackson Laboratories were used for all air pouch model (APM) studies. Mice were age-matched, six to eight weeks from start of experiment. All animals were maintained on a 24 hour light/dark cycle, with food and water available ad libitum. All experimental animal procedures were approved by and in accordance to the regulations of the Institutional Animal Care and Use Committee (IACUC) of Cephalon, Inc.

All spleen samples were analyzed using an Accuri C6 Flow Cytometer (Accuri Cytometers, Ann Arbor, Mich.). Antibodies used for western blot were anti-phosphorylated STAT5 (Cell Signaling Technology, Danvers, Mass.) and anti-total STAT5 (Cell Signaling Technology, Danvers, Mass.). Complete media (R10) was used for all experiments involving the ex vivo culture of splenocytes for all Elispot experiments. Complete media consisted of RPMI1640 (Cellgro, Manassas, Va.) plus 1% Pen-Strep (Cellgro, Manassas, Va.), 1% L-Gln (Cellgro, Manassas, Va.), 1% Non-essential amino acids (Cellgro, Manassas, Va.), β-Mercaptoethanol (Sigma, St Louis, Mo.), plus 10% FBS (Cellgro, Manassas, Va.). The small molecule JAK2 inhibitor, Compound A, was synthesized according to procedures detailed elsewhere [16]. Cell line, HEL92 (ATCC, Manassas, Va.), was used for early pharmacodynamic (PD) testing of pSTAT5 inhibition using Compound A.

Western Blots

Samples were heated at 70° C. for 10 minutes and loaded onto a NuPAGE 10% Bis-Tris Gel, 1.5 mm, 15 well (Invitrogen, Carlsbad, Calif.). The molecular weight marker used was a BioRad Kaleidoscope prestained standard (BioRad, Hercules, Calif.). Run conditions were 150 volts for 1 hour at room temperature (RT). Using semi-dry transfer apparatus (BioRad, Hercules, Calif.), proteins were transferred into a nitrocellulose membrane. Primary antibody diluted at 1:1000 in 5% milk for phosphorylated STAT3 pY705 (Cell Signaling Technology, Danvers, Mass.) and total STAT3 (Cell Signaling Technology, Danvers, Mass.) diluted to 1:1000 in 5%

BSA in TBS were incubated overnight at 4° C. with 5% milk in TBS plus 0.05% Tween-20. Anti-rabbit IgG, HRP-linked secondary antibody was used at 1:2000 (Cell Signaling Technology, Danvers, Mass.). Detection was performed using SuperSignal West Pico Chemiluminescent Substrate (Pierce, Rockford, Ill.). Densitometry was performed using GelPro analyzer 3.1 software.

Enzyme Assays

The kinase activity of baculovirus-expressed human JAK kinases (JAK1, JAK2, JAK3 or TYK2) was measured using the time-resolved fluorescence (TRF) detection system as described elsewhere [17]. Each 96-well Costar high binding plate (Corning, Corning, N.Y.) was coated with 100 µl/well of 10 µg/ml neutravidin (Pierce Biotechnology, Rockford, Ill.) in TBS at 37° C. for 2 h, followed by 100 µl/well of 1 µg/ml 15-mer peptide substrate (biotinyl-amino-hexanoyl-EQEDEPEGDYFEWLE-amide, Infinity Biotech Research and Resource, Aston, Pa.) at 37° C. for 1 h. The kinase assay mixture (total volume=100 µl/well) consisting of 20 mM HEPES (pH 7.2), ATP ($K_m$ level for each kinase), 1 mM $MnCl_2$, 0.1% BSA, and test Compound (diluted in DMSO; 2.5% DMSO final in assay) was added to the assay plate. The concentrations of ATP used were as follows: 0.2 µM ATP for JAK1, JAK2 and TYK2; 0.1 µM ATP for JAK3. Enzyme was added and the reaction was allowed to proceed for 20 min at RT. Detection of the phosphorylated product was performed by adding 100 µl/well of Eu-N1 labeled PY100 antibody (PerkinElmer Life Sciences, Boston, Mass.) diluted 1:5000 or 1:10000 in 0.25% BSA in TBS-T. Samples were incubated at RT for 1 h, followed by addition of 100 µl enhancement solution (PerkinElmer Life Sciences, Boston, Mass.). Plates were agitated for 10 min and the fluorescence of the resulting solution measured using the PerkinElmer EnVision® 2102 or 2104 multi-label plate reader. $IC_{50}$ values were determined using the 4-parameter logistic model in XLFit® 4 (IDBS, Ltd., Guildford, UK).

Collagen-Antibody Induced Arthritis (CAIA) Model

Acclimated mice were randomized, pre-bled and measured for baseline inflammation before any studies were initiated. On day 0, DBA/1 female mice were injected i.v. with 100 µl of a saline solution containing 1.5 mg of a 10 mg/ml cocktail of arthritogenic monoclonal antibodies directed against different epitopes of collagen type II (Chondrex, Redmond, Wash.) suspended in saline. On day 3, mice were injected with 100 µl of 50 µg of *E. coli* 0111:B4 LPS (0.5 mg/ml stock) (Chondrex, Redmond, Wash.) i.p. and provided with gel food during recovery. Two days post-LPS treatment monitoring of arthritic paws began; peak arthritis usually occurred 2-3 days following LPS treatment. Mice that exhibited a clinical score greater than "1" in each limb were considered arthritic and were entered into the study. Arthritis clinical score tables can be found described elsewhere [18]. Briefly, score '0' denotes no evidence of erythema and swelling; score '1' denotes erythema and mild swelling confined to the tarsus; score '2' denotes erythema and mild swelling extending from the ankle to mid-foot; score '3' denotes erythema and moderate swelling extending from the ankle to the metatarsal joints; score '4' denotes erythema and severe swelling encompassing the ankle, foot and digits. Vehicle consisted of PEG400 plus 1% DMSO provided orally, twice daily (b.i.d). Dexamethasone (Dex) (Hanna's Pharmaceutical Supply, Wilmington, Del.) at 1.5 mg/kg was administered i.p. three times a week in saline and continued from the peak of inflammation until the end of the experiment. Mice were cheek bled for serum sample collection for cytokines and antibodies throughout the experiment. All samples were kept at −80° C. until ready to assay. At about 4 weeks, mice were harvested for spleen, serum and arthritic paws for STAT and cytokine quantitation and histological analysis. For earlier validation, studies were ended around 3-4 weeks post induction and paws removed at various different time points to measure cytokine levels over time.

Collagen-Induced Arthritis (CIA) Model

Acclimated mice were randomized and pre-bled and measured for baseline inflammation before any studies were initiated. On day 0, DBA/1 female mice were given a primary immunization with equal volumes of bovine type II collagen (CII), 2 mg/ml stock in 0.05 M acetic acid, (Chrondrex, Redmond, Wash.) suspended in CFA, 5 mg/ml (Chondrex, Redmond, Wash.) emulsion yielding an injection of 100 µg of CII at 100 µl into the base of the tail intradermally (i.d.). At day 21 post primary immunization, mice were re-challenged with CII emulsified in Incomplete Freund's Adjuvant (IFA) (Thermo Scientific, Rockford, Ill.) s.c. on the flank of the mouse. On day 28 each mouse received an i.p. injection of *E. coli* 0111:B4 LPS (0.5 mg/ml stock) (Chondrex, Redmond, Wash.) at 10 µg in 100 µl of saline (25-50 µg of LPS was reduced to 10 µg per mouse to reduce mortality associated with endotoxic shock). Around day 35 the mice begin to show signs of paw inflammation and disease. Before starting treatment mice were randomized, grouped, scored, ear tagged and pre-bled to determine baseline disease. Mice that exhibited a clinical score greater than "1" in each limb were considered arthritic and were entered into the study. Arthritis clinical scores were the same as that used to score the CAIA model (see CAIA methods). Vehicle consisted of PEG400 plus 1% DMSO given orally, twice daily (b.i.d). Dexamethasone (Hanna's Pharmaceutical Supply, Wilmington, Del.) at 1.5 mg/kg was administered i.p. three times a week in saline and continued from the peak of inflammation until the end of the experiment. Mice were cheek bled for serum sample collection for cytokines and antibodies throughout the experiment. All samples were kept at −80° C. until ready to assay. At about day 60 mice were harvested for spleen, plasma and arthritic paws for STAT and cytokine quantitation and histological analysis.

Air Pouch Mouse Model for Carrageenan-Induced Inflammation

Details on the establishment and design of this rapid inflammation screening model can be found elsewhere [19, 20]. Briefly, Balb/c mice were injected s.c. with 4 ml of sterile air on day −5, baseline measurements were recorded and mice were randomized into groups. Mice entered the study upon air pouch maintenance by day −3 when 2 ml of sterile air is injected for air pouch maintenance. On day 0 mice were given a 1% carrageenan (Sigma, St. Louis, Mo.) injection suspended in saline directly into the air pouch. This induces a rapid inflammatory influx of primarily neutrophils and macrophage. The test compounds were provided in saline at mg/kg concentrations in 100 µl total volume and introduced directly into the air pouch simultaneously with the carrageenan injection, (1% carrageenan in saline). The induced inflammatory response was followed by a spike in IL-6, TNFα, IL-1β pouch cytokines and resolves by day 8. Twenty-four hours post-administration of carrageenan and the respective test compounds, 100 µl of air pouch fluid was removed along with cellular exudates. Cellular exudates were centrifuged, supernatants were processed for Luminex cytokine analysis, and the cell pellets were counted for total live and dead cells. Total cell counts were performed using BD Tru-Count beads (BD Biosciences, San Jose, Calif.) and cellular analysis was performed using 7-AAD (Sigma, St. Louis, Mo.) as a viability dye to exclude dead cells. Hemoglobin content was determined using the Drabkin's assay (Sigma, St. Louis, Mo.).

Histology-CAIA and CIA Arthritis Models

At the end of each experiment, front and hind paws (including carpus and tarsus) were removed from the body of the animal for histological analysis. Skin from the ends of the digits was removed and the metatarsal region skin perforated using surgical scissors to allow full decalcification. Samples followed a decalcification procedure using formic acid as described elsewhere [21, 22]. After 7-10 days of decalcification, samples were washed for 2 hours in distilled water and stored in 70% ethanol at 4° C. until ready to be processed. Samples were paraffin embedded, sectioned and stained with Hematoxylin and Eosin (H&E) stain, also Safranin-O for matrix degradation (images not shown, used by pathologist for scoring). All histology work was performed at the Wistar Institute (Philadelphia, Pa.). Images were collected using an Olympus BX50 scope with an Olympus DP70 camera and Olympus LabSens software (2009). A total of five mice from each group were analyzed via histopathology, 10× representative images are shown for each group tested.

Measurement of Serum Anti-Collagen Type I and Type II Autoantibodies

Serum was collected every 1-2 weeks and stored at −80° C. until use. Thawed samples were analyzed by an in-house generated collagen type II and type I ELISA method. Briefly each well of a 96-well plate was coated with 50 µl of 5 µg/ml of collagen type I (Chondrex, Redmond, Wash.) or collagen type II (Chondrex, Redmond, Wash.) in BBS (0.025M $Na_2B_4O_7$-$10H_2O$, 0.01M $H_3BO_3$, 0.075M NaCl, pH 8.4) buffer overnight at 4° C. Plates were washed with BBS plus 0.1% Tween-20 three times before proceeding. Standard curves were generated using purified mouse anti-collagen type I or type II antibody, serum was added at 50 µl per well, incubated at room temperature (RT) for 1 hour then washed with BBS plus Tween-20. After washing, 50 µl of 1 µg/ml of a rabbit anti-mouse HRP-Fab fragment was added as a detection antibody (Rockland, Gilbertsville, Pa.) and incubated at RT for 45 minutes. Plates were washed four times with BBS plus Tween-20, then 100 µl of tetramethylbenzidine (TMB) substrate was added and the reaction was stopped using 100 µl of 1M $H_2SO_4$. The plates were read at 450 nm with a reference wavelength of 570 nm.

Elispots

Both T and B cell Elispot methods can be found elsewhere [23, 24], briefly the technique for each is described here.

T-Cell Elispots

For CIA experiments, Millipore nitrocellulose IP filter plates (Millipore, Billerica, Mass.) were coated with either anti-mouse IFNγ (AN18, MabTech, Mariemont, Ohio) or anti-mouse IL-4 (11B11, eBioscience, San Diego, Calif.) at 7 µg/ml or 2 µg/ml, respectively, in sterile PBS at 60 µl per well and incubated for 3 hours at RT or overnight at 4° C. Coated wells were washed with PBS plus 0.1% Tween-20 and patted semi-dry before blocking using complete media for at least 1 hour before use. Purified mouse collagen type II (Chrondrex, Redmond, Wash.), type I (Chrondrex, Redmond, Wash.) or third party control chicken ovalbumin (OVA) (Sigma, St. Louis, Mo.) were used to challenge 1 million processed splenocytes per well at 10 µg/ml of total antigen concentration. Media alone were used as background controls, OVA as third party controls and PMA plus Ionomycin as positive controls for IFNγ and IL-4 release by Th1 and Th2 cells, respectively.

B-Cell Elispot

B-cell Elispot components were obtained from MabTech and nitrocellulose IP filter plates were obtained from Millipore. Briefly, for CIA experiments B-cell Elispot wells were activated using ethanol, then washed and coated with 10 µg/ml of purified bovine collagen type II or I (Chrondrex, Redmond, Wash.) in sterile PBS; OVA was used as a third party control and media alone for background. Processed splenocytes were added to each well and were not stimulated with LPS to avoid true ex vivo frequencies of antibody secreting cell types (ASCs). Anti-mouse total IgG was used as a positive control for total IgG producing ASCs and was used to normalize results. Cell frequencies for detection of each antigen were previously identified during optimization and validation phases for each model tested (data not shown). A total of 500,000 cells were added to each well for the CI and CII coated wells for CIA experiments. B-cell Elispots were incubated overnight at 37° C., 5% $CO_2$. To develop each assay, secondary antibody (MabTech, Mariemont, Ohio) was added to each well, incubated, washed, alkaline phosphatase streptavidin used as conjugate (Jackson Immunoresearch, West Grove, Pa.), BCIP-NBT (Rockland Biologicals, Gilbertsville, Pa.) used as a substrate, and developed until spots were visible. All Elispot analyses were performed using an Immunospot C.T.L. scanner and Biospot software (2009).

Measurement of Serum Cytokines Via Multiplex Luminex® Bead Assays

Frozen plasma at −80° C. was thawed on ice, vortexed, then centrifuged for 10 minutes to remove debris and aggregates. A total of 25-50 µl of serum was used for Luminex® assays following the manufacturer's instruction. Ten different mouse cytokines were measured using the mouse cytokine 10-plex bead kit (Invitrogen, Carlsbad, Calif.). Briefly, filter plates (Millipore, Billerica, Mass.), were pre-wet with 200 µl of wash solution (kit component) and 25 µl of beads were added per well. Serum samples were diluted and a total volume of 50 µl was added per well (i.e., 25 µl of sample serum plus 25 µl of assay diluent). Plates with beads were incubated for 2 hours at RT on an orbital shaker in the dark. At the end of the incubation the plates were washed twice in buffer, secondary biotinylated antibody was added at a 1:10 dilution, 100 µl, in biotin diluent provided with the kit. Plates were incubated at RT for 1 hour in the dark then washed twice in buffer. Streptavidin in assay diluent was added at 100 µl per well, then incubated at 30 minutes at RT in the dark. Plates were washed three times with 100 µl of wash solution and agitated for 2-3 minutes at RT in the dark. Plates were run immediately on a Luminex xMAP 200 unit with data acquisition and analysis software (Invitrogen, Carlsbad, Calif.). All bead washing was performed using a vacuum manifold unit (Pall, Port Washington, NY).

Measurement of Paw Cytokines and Phospho-STATs Via Multiplex Luminex® Bead Assays A more detailed description of this method can be found described elsewhere (Lu et al, 2010, submitted for publication). Briefly, the front (including carpus) and back (including tarsus) right paws were collected and frozen in dry-ice cooled isopentane and stored at −80° C. until use. The paws were cut to 2 mm×2 mm segments and kept on dry-ice in round bottom polypropylene tubes. Seven hundred microliters tissue extraction buffer containing protease inhibitor cocktail (Calbiochem, San Diego, Calif.) and Halt phosphatase inhibitor cocktail (Thermo Scientific, Rockford, Ill.) or Roche phosphatase inhibitor cocktail (Roche, Indianapolis, Ind.) in tissue extraction reagent I (Invitrogen, Carlesbad, Calif.) were added to each sample. Samples were homogenized frozen using a PT 10-35 Polytron homogenizer. After homogenization, samples were centrifuged at 4° C. for 2000×g for 10 minutes and supernatants re-centrifuged at 4° C. at maximum speed, 14,000×g, for 15 minutes. Supernatants were carefully removed to avoid picking up the top layer of lipids/adipose debris. Protein concentration was measured using a BCA protein assay (Pierce, Rockford, Ill.) and adjusted to 3 mg/ml.

A minimum of 25 µl of this extraction was used in the above described protocol using the mouse cytokine 10-plex bead kit (Invitrogen, Carlsbad, Calif.) or phosphorylated STAT1, 3, 5a/b, 3-plex kit (Invitrogen, Carlsbad, Calif.).

Compound Quantification (PK, Pharmacokinetics)

Plasma and protein extraction from paw and spleen samples were submitted for quantitative analysis to determine the respective compound concentrations. Blood samples were collected into heparinized tubes and placed on wet ice until centrifuged (16,000×g, 5 minutes) to separate the plasma. Supernatant was collected and stored at −20° C. pending analysis. At the time of analysis, two volumes of cold acetonitrile containing an internal standard (alprenolol) were added to each sample which were then vortexed and centrifuged. The supernatants were removed, placed into an autosampler vial and the amount of compound present in the samples was analyzed by liquid chromatograph/mass spectrometry (LC-MS-MS). The concentration of compound in the samples was quantified against a mouse plasma standard curve made via serial dilution in a concentration range from 5 to 20,000 ng/mL. Samples containing concentrations greater than 10% above the top of the standard curve were diluted 1:10 with acetonitrile. The limit of detection for plasma, paw and spleen were <10 ng/ml.

Statistical Analysis

All ELISA or Luminex® assays were analyzed using linear regression curves to determine concentration of analyte following data acquisition. Mann-Whitney non-parametric, 1- or 2-way ANOVA were used as statistical tests where noted in figure legends depending on the experiment and tested hypothesis. A p-value less than 0.05 was considered significant. Statistical software used was Graph Pad Prism (vs. 5.01, 2007), calculations were performed using Microsoft Office Excel (Professional, 2003).

Reported here is the efficacy profile of COMPOUND A, a highly selective, orally active, small molecule inhibitor of JAK2 which was evaluated in two mouse models of RA. Pharmacodynamic inhibition of JAK2 reduced mean paw edema and clinical scores in both CIA and CAIA models of arthritis. Reduction in paw and serum cytokines correlated with reduced spleen CII-specific Th1 cell frequencies as measured by ex vivo IFNγ Elispot. Both models demonstrated histological evidence of disease amelioration upon treatment and reduced paw pSTAT3 levels. This study demonstrates the utility of using a potent and highly selective, orally bioavailable JAK2 inhibitor for the treatment of RA.

The CIA model is dependent on both T and B cell responses and, as in human RA, depends on the action of IL-6, demonstrating that Compound A could modulate key immune cytokines involved in human disease [15, 37, 38]. Unlike the CIA model, the CAIA model has shown to be not entirely dependent on IL-6 as mice deficient in this cytokine can still be induced for arthritis [39]. However, surprisingly, robust activity of Compound A is observed in the CAIA model, sometimes exceeding that of the standard of care agent Dex. The use of tocilizumab demonstrates how targeting cytokines can directly impact disease progression without overt immunosuppression [8]. Other small molecules such as INCB028050 have also been reported to show a similar phenotype, i.e. inhibition of IL-6 and disease without immunosuppression [14]. It is possible that Compound A is working similar to INCB028050 as both can inhibit immune cellular flux and cytokine release in acute inflammation mouse models (i.e., delayed-type hypersensitivity for INCB028050 and APM model for Compound A).

JAK2 is responsible for mediating signaling through several receptors including those highly implicated in playing an essential role in autoimmunity and inflammation such as the gp130 receptor family, IL-6R and IL-12Rβ and IFNγR2 [40]. In addition, JAK2 mediates signaling through several components of the GM-CSF receptor superfamily (e.g., IL-3R, IL-5R, GM-CSF-R). JAK2 also controls single chain receptors such as the erythropoietin receptor (Epo-R), thrombopoietin receptor (Tpo-R), growth hormone receptor (GH-R), prolactin receptor (PRL-R) and leptin receptor (LR). Leptin is structurally similar to IL-2 and IL-15 and has been implicated to play a role in immunity [41]. Since JAK2 mediates signaling from LR, inhibition of JAK2 may act as a possible target for inflammatory diseases with clear cardiovascular links such as arterio- and atherosclerosis [42].

Interactions of JAK2 with various immune-related signaling molecules will determine how inhibition of this kinase may impact other immune cell types and thus treatment of other autoinflammatory diseases. Downstream, JAK2 can interact with STAT5a/b, STAT3, STAT4 and STAT1 [43]. However, only STAT5a/b are directly activated by JAK2; STAT4 can be activated via TYK2, STAT1 via JAK1, and STAT3 can be activated via the EGFR pathway, JAK1 and Src kinases [27, 28]. In addition, several kinases including Tec, Vav1, Fyn, Yes1 and PTK2 also directly interact with JAK2 [44-48]. These kinases are all involved, at some level, in the regulation and activation of immune subsets, especially that of T and B lymphocytes. Inhibiting JAK2 may have further implications than just direct inhibition of cytokine signaling. Downstream inhibition of T and B-cell activation may also result from JAK2 inhibition, expanding the possibilities of using a potent inhibitor of this kinase in alternate indications.

For example, kinases controlling lymphocyte activation includes the Tec family of tyrosine kinases and includes Itk and Btk kinase that interacts with molecules like Vav1 on adaptor molecule islands SLP76 in T-cells and BLNK in B-cells [49]. Primarily Tec kinases are responsible for proper T-cell receptor signaling and activation. Mice deficient in the Tec kinase Itk fail to effectively differentiate into Th2 effector cells and mice lack the ability to mount a defense against invading extracellular parasites and also some viral infections [50]. Itk deficient mice also exhibit a decrease in lung infiltration of T cells in a mouse model of asthma [51]. Downstream molecule, Vav1, transmits TCR and CD28 signals to CRE via PKC and ERK responsible for T-cell activation [52]. Potential JAK2 downstream targets Fyn and Yes1 play important roles in T and B cell activation and inhibition of either may affect the downstream threshold needed for lymphocyte activation [53]. Thus, full or partial inhibition of any of these above mentioned kinases via the inhibition of JAK2 activity could greatly impact the initiation and progression of several autoimmune diseases. Further investigation is warranted for the use of this potent inhibitor in other inflammatory diseases.

Suppressors of JAK-STAT signaling, SOCS, also interact directly with JAK2 (e.g., SOCS3) [43, 54]. SOCS proteins act as a negative feed back loop for the JAK-STAT pathway [55]. Interestingly, the expression of SOCS is altered in RA patients; levels of SOCS1 and SOCS3 were showed to be increased in PBMCs from RA patients [56]. SOCS1 was upregulated in peripheral blood T cells associated with SOCS3-expression in peripheral blood monocytes in patients with RA [56]. SOCS1 was also showed to be upregulated in the synovial membranes from patients with RA compared to patients with osteoarthritis. This suggests that deregulation of JAK2 signaling via effects on SOCS can contribute to RA development and may predict a patient's susceptibility to disease development.

Inhibition of disease-promoting cytokine pathways by Compound A rivaled the results measured using standard of care treatments; strongly suggesting the use of this inhibitor in other IL-6-dependent diseases such Crohn's Disease and ulcerative colitis. Compound A may also have utility in other diseases dependent on those same pathways such as SLE, IBD, psoriasis and various cancers including colon, prostate and pancreatic cancer. These results warrant further preclinical evaluation of selective JAK2 inhibitors such as Compound A.

Those skilled in the art will readily appreciate that the specific experiments detailed herein are only illustrative of the various aspects of the invention. It should be understood that numerous modifications can be made without departing from the spirit and scope of this application.

References

The following scientific papers are referenced above so as to more fully describe the state of the art to which this application pertains. Full citations for these references are provided below.

1. Nathan C, Ding A: Nonresolving inflammation. *Cell* 2010, 140(6):871-882.
2. Kundu J K, Surh Y J: Inflammation: gearing the journey to cancer. *Mutat Res* 2008, 659(1-2):15-30.
3. Chan A C, Carter P J: Therapeutic antibodies for autoimmunity and inflammation. *Nat Rev Immunol* 2010, 10(5): 301-316.
4. Opar A: Kinase inhibitors attract attention as oral rheumatoid arthritis drugs. *Nat Rev Drug Discov* 2010, 9(4):257-258.
5. Cohen S, Fleischmann R: Kinase inhibitors: a new approach to rheumatoid arthritis treatment. *Curr Opin Rheumatol* 2010, 22(3):330-335.
6. Bajpai M: Fostamatinib, a Syk inhibitor prodrug for the treatment of inflammatory diseases. *IDrugs* 2009, 12(3): 174-185.
7. Bingham C O, 3rd: Emerging therapeutics for rheumatoid arthritis. *Bull NYU Hosp Jt Dis* 2008, 66(3):210-215.
8. Oldfield V, Dhillon S, Plosker G L: Tocilizumab: a review of its use in the management of rheumatoid arthritis. *Drugs* 2009, 69(5):609-632.
9. Kerbleski J F, Gottlieb A B: Dermatological complications and safety of anti-TNF treatments. *Gut* 2009, 58(8):1033-1039.
10. Williams E L, Gadola S, Edwards C J: Anti-TNF-induced lupus. *Rheumatology (Oxford)* 2009, 48(7):716-720.
11. Ramos-Casals M, Brito-Zeron P, Soto M J, Cuadrado M J, Khamashta M A: Autoimmune diseases induced by TNF-targeted therapies. *Best Pract Res Clin Rheumatol* 2008, 22(5):847-861.
12. Walker J G, Smith M D: The Jak-STAT pathway in rheumatoid arthritis. *J Rheumatol* 2005, 32(9):1650-1653.
13. West K: CP-690550, a JAK3 inhibitor as an immunosuppressant for the treatment of rheumatoid arthritis, transplant rejection, psoriasis and other immune-mediated disorders. *Curr Opin Investig Drugs* 2009, 10(5):491-504.
14. Fridman J S, Scherle P A, Collins R, Burn T C, Li Y, Li J, Covington M B, Thomas B, Collier P, Favata M F et al: Selective inhibition of JAK1 and JAK2 is efficacious in rodent models of arthritis: preclinical characterization of INCB028050. *J Immunol* 2010, 184(9):5298-5307.
15. Uchiyama Y, Yorozu K, Hashizume M, Moriya Y, Mihara M: Tocilizumab, a humanized anti-interleukin-6 receptor antibody, ameliorates joint swelling in established monkey collagen-induced arthritis. *Biol Pharm Bull* 2008, 31(6): 1159-1163.
16. Curry M, Dorsey, B., Dugan, B., Gingrich, D., Mesaros, E., Mikiewicz, K.: Preparation and Uses of 1,2,4-Triazolo[1,5a]Pyridine Derivatives. Cephalon, Inc.; Filed: Jun. 4, 2010.
17. Hexner E O, Serdikoff C, Jan M, Swider C R, Robinson C, Yang S, Angeles T, Emerson S G, Carroll M, Ruggeri B et al: Lestaurtinib (CEP701) is a JAK2 inhibitor that suppresses JAK2/STAT5 signaling and the proliferation of primary erythroid cells from patients with myeloproliferative disorders. *Blood* 2008, 111(12):5663-5671.
18. Brand D D, Kang A H, Rosloniec E F: The mouse model of collagen-induced arthritis. *Methods Mol Med* 2004, 102: 295-312.
19. Romano M, Faggioni R, Sironi M, Sacco S, Echtenacher B, Di Santo E, Salmona M, Ghezzi P: Carrageenan-induced acute inflammation in the mouse air pouch synovial model. Role of tumour necrosis factor. *Mediators Inflamm* 1997, 6(1):32-38.
20. Ellis L, Gilston V, Soo C C, Morris C J, Kidd B L, Winyard P G: Activation of the transcription factor NF-kappaB in the rat air pouch model of inflammation. *Ann Rheum Dis* 2000, 59(4):303-307.
21. Verdenius H H, Alma L: A quantitative study of decalcification methods in histology. *J Clin Patrol* 1958, 11(3): 229-236.
22. Egger F M, Germaine J P: Rapid demineralization in acidic buffers. *Photochemistry* 1979, 59(3):215-224.
23. Peavey M M, Maciag P C, Al-Rawi N, Sewell D, Paterson Y: An anti-vascular endothelial growth factor receptor 2/fetal liver kinase-1 *Listeria monocytogenes* anti-angiogenesis cancer vaccine for the treatment of primary and metastatic Her-2/neu+ breast tumors in a mouse model. *J Immunol* 2009, 182(9):5537-5546.
24. Vingsbo C, Larsson P, Andersson M, Holmdahl R: Association of pepsin with type II collagen (CII) breaks control of CII autoimmunity and triggers development of arthritis in rats. *Scand J Immunol* 1993, 37(3):337-342.
25. Fabian M A, Biggs W H, 3rd, Treiber D K, Atteridge C E, Azimioara M D, Benedetti M G, Carter T A, Ciceri P, Edeen P T, Floyd M et al: A small molecule-kinase interaction map for clinical kinase inhibitors. *Nat Biotechnol* 2005, 23(3):329-336.
26. Karaman M W, Herrgard S, Treiber D K, Gallant P, Atteridge C E, Campbell B T, Chan K W, Ciceri P, Davis M I, Edeen P T et al: A quantitative analysis of kinase inhibitor selectivity. *Nat Biotechnol* 2008, 26(1):127-132.
27. Turkson J, Bowman T, Garcia R, Caldenhoven E, De Groot R P, Jove R: Stat3 activation by Src induces specific gene regulation and is required for cell transformation. *Mol Cell Biol* 1998, 18(5):2545-2552.
28. Lo H W, Hsu S C, Ali-Seyed M, Gunduz M, Xia W, Wei Y, Bartholomeusz G, Shih J Y, Hung M C: Nuclear interaction of EGFR and STAT3 in the activation of the iNOS/NO pathway. *Cancer Cell* 2005, 7(6):575-589.
29. Kang I, Lee W W, Lee Y: Modulation of collagen-induced arthritis by IL-4 and dexamethasone: the synergistic effect of IL-4 and dexamethasone on the resolution of CIA. *Immunopharmacology* 2000, 49(3):317-324.
30. Montesinos M C, Desai A, Cronstein B N: Suppression of inflammation by low-dose methotrexate is mediated by adenosine A2A receptor but not A3 receptor activation in thioglycollate-induced peritonitis. *Arthritis Res Ther* 2006, 8(2):R53.
31. Douni E, Sfikakis P P, Haralambous S, Fernandes P, Kollias G: Attenuation of inflammatory polyarthritis in TNF transgenic mice by diacerein: comparative analysis with dexamethasone, methotrexate and anti-TNF protocols. *Arthritis Res Ther* 2004, 6(1):R65—R72.
32. Lu L D, Stump, K. L., Peavey, M. M.: Novel Method of Monitoring Trace Cytokines and Activated STAT Molecules in the Paws of Arthritic Mice using Multiplex Bead Technology. *Journal of Immunological Methods* 2010, in review.
33. McInnes I B, Schett G: Cytokines in the pathogenesis of rheumatoid arthritis. *Nat Rev Immunol* 2007, 7(6):429-442.
34. Cornelissen F, van Hamburg J P, Lubberts E: The IL-12/IL-23 axis and its role in Th17 cell development, pathology and plasticity in arthritis. *Curr Opin Investig Drugs* 2009, 10(5):452-462.
35. Singh R, Aggarwal A, Misra R: Th1/Th17 cytokine profiles in patients with reactive arthritis/undifferentiated spondyloarthropathy. *J Rheumatol* 2007, 34(11):2285-2290.
36. Calero I, Nieto J A, Sanz I: B Cell Therapies for Rheumatoid Arthritis: Beyond B cell Depletion. *Rheum Dis Clin North Am* 2010, 36(2):325-343.
37. Alonzi T, Fattori E, Lazzaro D, Costa P, Probert L, Kollias G, De Benedetti F, Poli V, Ciliberto G: Interleukin 6 is required for the development of collagen-induced arthritis. *J Exp Med* 1998, 187(4):461-468.
38. Sasai M, Saeki Y, Ohshima S, Nishioka K, Mima T, Tanaka T, Katada Y, Yoshizaki K, Suemura M, Kishimoto T: Delayed onset and reduced severity of collagen-induced arthritis in interleukin-6-deficient mice. *Arthritis Rheum* 1999, 42(8):1635-1643.
39. Kagari T, Doi H, Shimozato T: The importance of IL-1 beta and TNF-alpha, and the noninvolvement of IL-6, in the development of monoclonal antibody-induced arthritis. *J Immunol* 2002, 169(3):1459-1466.
40. Fonseca J E, Santos M J, Canhao H, Choy E: Interleukin-6 as a key player in systemic inflammation and joint destruction. *Autoimmun Rev* 2009, 8(7):538-542.
41. Procaccini C, Lourenco E V, Matarese G, La Cava A: Leptin signaling: A key pathway in immune responses. *Curr Signal Transduct Ther* 2009, 4(1):22-30.
42. La Cava A, Matarese G: The weight of leptin in immunity. *Nat Rev Immunol* 2004, 4(5):371-379.
43. O'Shea J J, Murray P J: Cytokine signaling modules in inflammatory responses. *Immunity* 2008, 28(4):477-487.
44. Takahashi-Tezuka M, Hibi M, Fujitani Y, Fukada T, Yamaguchi T, Hirano T: Tec tyrosine kinase links the cytokine receptors to PI-3 kinase probably through JAK. *Oncogene* 1997, 14(19):2273-2282.
45. Shigematsu H, Iwasaki H, Otsuka T, Ohno Y, Arima F, Niho Y: Role of the vav proto-oncogene product (Val) in erythropoietin-mediated cell proliferation and phosphatidylinositol 3-kinase activity. *J Biol Chem* 1997, 272(22):14334-14340.
46. Sayeski P P, Ali M S, Safavi A, Lyles M, Kim S O, Frank S J, Bernstein K E: A catalytically active Jak2 is required for the angiotensin II-dependent activation of Fyn. *J Biol Chem* 1999, 274(46):33131-33142.
47. Fuhrer D K, Yang Y C: Complex formation of JAK2 with PP2A, P13K, and Yes in response to the hematopoietic cytokine interleukin-11. *Biochem Biophys Res Commun* 1996, 224(2):289-296.
48. Ryu H, Lee J H, Kim K S, Jeong S M, Kim P H, Chung H T: Regulation of neutrophil adhesion by pituitary growth hormone accompanies tyrosine phosphorylation of Jak2, p125FAK, and paxillin. *J Immunol* 2000, 165(4):2116-2123.
49. Bradshaw J M: The Src, Syk, and Tec family kinases: distinct types of molecular switches. *Cell Signal* 2010, 22(8):1175-1184.
50. Fowell D J, Shinkai K, Liao X C, Beebe A M, Coffman R L, Littman D R, Locksley R M: Impaired NFATc translocation and failure of Th2 development in Itk-deficient CD4+ T cells. *Immunity* 1999, 11(4):399-409.
51. Mueller C, August A: Attenuation of immunological symptoms of allergic asthma in mice lacking the tyrosine kinase ITK. *J Immunol* 2003, 170(10):5056-5063.
52. Haubert D, Weckbecker G: Vav1 couples the T cell receptor to cAMP response element activation via a PKC-dependent pathway. *Cell Signal* 2010, 22(6):944-954.
53. Sefton B M, Taddie J A: Role of tyrosine kinases in lymphocyte activation. *Curr Opin Immunol* 1994, 6(3): 372-379.
54. Haan S, Wuller S, Kaczor J, Rolvering C, Nocker T, Behrmann I, Haan C: SOCS-mediated downregulation of mutant Jak2 (V617F, T875N and K539L) counteracts cytokine-independent signaling. *Oncogene* 2009, 28(34): 3069-3080.
55. Ying M, Li D, Yang L, Wang M, Wang N, Chen Y, He M, Wang Y: Loss of SOCS3 expression is associated with an increased risk of recurrent disease in breast carcinoma. *J Cancer Res Clin Oncol* 2010.
56. Isomaki P, Alanara T, Isohanni P, Lagerstedt A, Korpela M, Moilanen T, Visakorpi T, Silvennoinen O: The expression of SOCS is altered in rheumatoid arthritis. *Rheumatology (Oxford)* 2007, 46(10):1538-1546.

The invention claimed is:

1. A method of treating rheumatoid arthritis comprising:
   identifying a subject affected by rheumatoid arthritis, and
   administering to said subject a therapeutically effective amount of Compound A:

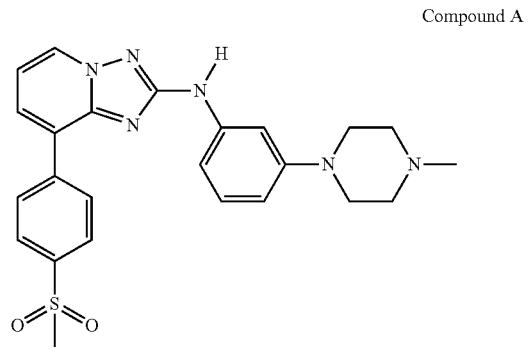 [SMILES: CN1CCN(c2cccc(Nc3nc4c(-c5ccc(S(C)(=O)=O)cc5)cccn4n3)c2)CC1]

Compound A or a salt thereof.

2. A method of treating chronic systemic inflammation comprising:
   identifying a subject affected by chronic systemic inflammation, and
   administering to said subject a therapeutically effective amount of Compound A:

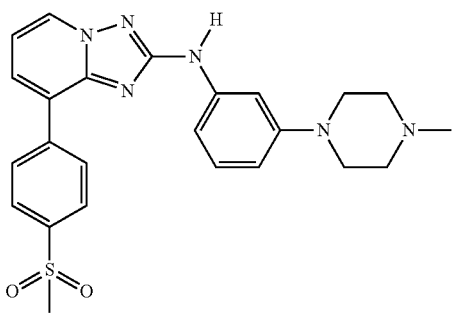

Compound A or a salt thereof.

3. A method for reducing at least one symptom of chronic systemic inflammation in a subject comprising administering Compound A:

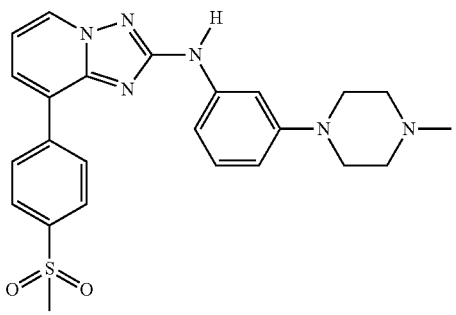

Compound A or a salt thereof, in an amount effective to inhibit JAK2 kinase.

4. The method according to claim 1 wherein the Compound A or salt thereof is administered in an amount of about 0.1 mg/kg to about 300 mg/kg.

5. The method according to claim 4 wherein the Compound A or salt thereof is administered in an amount of about 30 mg/kg to about 100 mg/kg.

6. The method according to claim 1 wherein the Compound A or salt thereof is administered up to four times per day.

7. The method according to claim 6 wherein the Compound A or salt thereof is administered two times per day.

8. The method according to claim 7 wherein the Compound A or salt thereof is administered in an amount of about 100 mg/kg.

9. The method according to claim 7 wherein the Compound A or salt thereof is administered in an amount of about 55 mg/kg.

10. The method according to claim 1 wherein the Compound A or salt thereof is administered orally.

11. The method according to claim 1 wherein the subject is human.

12. The method according to claim 2 wherein the Compound A or salt thereof is administered in an amount of about 0.01 mg/kg to about 1500 mg/kg per day.

13. The method according to claim 2 wherein the Compound A or salt thereof is administered up to four times per day.

14. The method according to claim 3 wherein the Compound A or salt thereof is administered in an amount of about 0.01 mg/kg to about 1500 mg/kg per day.

15. The method according to claim 3 wherein the Compound A or salt thereof is administered up to four times per day.

* * * * *